United States Patent
Tomiyama et al.

(10) Patent No.: US 12,415,834 B2
(45) Date of Patent: Sep. 16, 2025

(54) GhR-BINDING PEPTIDE AND COMPOSITION COMPRISING SAME

(71) Applicant: PEPTIDREAM INC., Kanagawa (JP)

(72) Inventors: Tatsuya Tomiyama, Kanagawa (JP);
Haruaki Kurasaki, Kanagawa (JP);
Katsuma Matsui, Kanagawa (JP);
Yoshiaki Masuda, Kanagawa (JP);
Masataka Umitsu, Kanagawa (JP)

(73) Assignee: PeptiDream Inc., Kanagawa (JP)

( * ) Notice: Subject to any disclaimer, the term of this patent is extended or adjusted under 35 U.S.C. 154(b) by 0 days.

(21) Appl. No.: 17/842,953

(22) Filed: Jun. 17, 2022

(65) Prior Publication Data

US 2023/0012823 A1    Jan. 19, 2023

Related U.S. Application Data

(60) Provisional application No. 63/212,596, filed on Jun. 18, 2021.

(51) Int. Cl.
*C07K 7/64* (2006.01)
*A61K 38/00* (2006.01)
*C07K 7/08* (2006.01)

(52) U.S. Cl.
CPC ............. *C07K 7/64* (2013.01); *C07K 7/08* (2013.01); *A61K 38/00* (2013.01)

(58) Field of Classification Search
None
See application file for complete search history.

(56) References Cited

U.S. PATENT DOCUMENTS

| 2008/0103293 | A1 | 5/2008 | Cho et al. |
| 2013/0180001 | A1* | 7/2013 | Vielle-Calzada ............... C12N 15/8287 800/278 |

OTHER PUBLICATIONS

Neggers Sebastian J.C.M.M et al., Pegvisomant Treatment in Acromegaly, Neuroendocrinology., vol. 103, No. 1, Mar. 19, 2015, pp. 59-65.

Basu Reetobrata et al., "A novel peptide antagonist of the human growth hormone receptor", Journal of Biological Chemistry, vol. 296, Jan. 1, 2021, pp. 100588.

* cited by examiner

*Primary Examiner* — Sergio Coffa
(74) *Attorney, Agent, or Firm* — Knobbe, Martens, Olson & Bear, LLP

(57) ABSTRACT

The present technology generally relates to peptides that bind to the growth hormone receptor (GhR), to peptides that bind to the GhR and have antagonistic activity, and to compositions comprising such peptides.

17 Claims, 2 Drawing Sheets
Specification includes a Sequence Listing.

FIG. 1

| Peptide SEQ ID No. | 1 X1 | 2 X2 | 3 X3 | 4 X4 | 5 X5 | 6 X6 | PEPTIDE SEQ 7 X7 | 8 X8 | 9 X9 | 10 X10 | 11 X11 | 12 X12 | 13 X13 |
|---|---|---|---|---|---|---|---|---|---|---|---|---|---|
| 1 | Y | MeK | V | V | S | N | W1aa | Y | K | W5H | Aib | V | C |
| 2 | Y | MeK(G) | V | V | S | N | W1aa | Y | K | W5H | Aib | V | C |
| 3 | Y | MeK(iMeG) | V | V | S | N | W1aa | Y | K | W5H | Aib | V | C |
| 4 | Y | MeK(P) | V | V | S | N | W1aa | Y | K | W5H | Aib | V | C |
| 5 | F4COO | MeK | V | V | S | N | W1aa | Y | K | W5H | Aib | V | C |
| 6 | F4COO | MeK | V | V | S | N | W1aa | F4COO | Hgn | W5H | Aib | V | C |
| 7 | F4COO | MeK | V | V | S | N | W1aa | F4COO | Ahp | W5H | Aib | V | C |
| 8 | F4COO | MeK | V | V | S | N | W1aa | F4COO | Har | W5H | Aib | V | C |
| 9 | F4COO | MeK | V | V | S | N | W1aa | F4COO | K | W5H | A4pipaa | V | C |
| 10 | F4COO | MeK | V | V | S | N | W1aa | F4COO | K | W5H | Aib | V | C |
| 11 | F4COO | MeK | V | V | S | N | W1aa | Y | KCOpipzaa | W5H | Aib | V | C |
| 12 | F4COO | MeK | V | V | S | N | W1aa | Y | K | W5H | A4pipaa | V | C |
| 13 | F4COO | MeK | V | V | S | N | W1aa | Y | K | W5H | Aib | V | C |
| 14 | 3Py6COO | MeK | V | V | S | N | W1aa | 3Py6COO | K | W5H | Aib | V | C |
| 15 | Y | MeK | V | V | S | N | W1aa | F4COO | KCOpipzaa | W5H | Aib | V | C |
| 16 | Y | MeK | V | V | S | N | W1aa | F4COO | K | W5H | A4pipaa | V | C |
| 17 | Y | MeK | V | V | S | N | W1aa | Y | KCOpipzaa | W5H | Aib | V | C |
| 18 | Y | MeK | V | V | S | N | W1aa | Y | K | W5H | A4pipaa | V | C |
| 19 | Y | MeK | V | V | S | N | W7N | F4COO | K | W5H | Aib | V | C |
| 20 | 4Py | MeK | V | V | S | N | W7N | F4COO | K | W5H | Aib | V | C |
| 21 | 4Py | MeK | V | V | S | N | W5OMe | F4COO | K | W5H | Aib | V | C |
| 22 | F4COO | MeK | V | V | S | N | W5OMe | F4COO | KCOpipzaa | W5H | Aib | V | C |
| 23 | F4COO | MeK | V | V | S | N | W5OMe | F4COO | K | W5H | A4pipaa | V | C |
| 24 | F4COO | MeK | V | V | S | N | W5OMe | F4COO | K | W5H | Aib | V | C |
| 25 | Y | MeK | V | V | S | N | W7N | Y | K | W5H | Aib | V | C |
| 26 | Y | MeK | V | V | S | N | W5OMe | Y | KCOpipzaa | W5H | Aib | V | C |
| 27 | Y | MeK | V | V | S | N | W5OMe | Y | K | W5H | A4pipaa | V | C |
| 28 | Y | MeK | V | V | S | N | W5OMe | Y | K | W5H | Aib | V | C |
| 29 | Y | MeK | V | V | S | N | W5OMe | F4COO | KCOpipzaa | W5H | Aib | V | C |
| 30 | Y | MeK | V | V | S | N | W5OMe | F4COO | K | W5H | A4pipaa | V | C |
| 31 | Y | MeK | V | V | S | N | W5OMe | F4COO | K | W5H | Aib | V | C |

| Peptide SEQ ID No. | LINKER PEPTIDE SEQ | | | | | |
|---|---|---|---|---|---|---|
| | 1 | 2 | 3 | 4 | 5 | 6 |
| | K | | | | | |
| | G | | | | | |
| 32 | G | P | ds | ds | ds | |
| 33 | G | P | ds | ds | ds | K |

FIG. 2

GhR-BINDING PEPTIDE AND COMPOSITION COMPRISING SAME

CROSS-REFERENCE TO RELATED APPLICATION

This application claims the benefit of and priority to U.S. provisional patent application No. 63/212,596, filed on Jun. 18, 2021, the content of these applications is herein incorporated in its entirety by reference.

ELECTRONIC FILE—SEQUENCE LISTING

This application hereby incorporates by reference the material of the electronic Sequence Listing filed concurrently herewith. The material in the electronic Sequence Listing is submitted as a text (.txt) file entitled "100964-48-Sequence Listing.txt" created on Aug. 15, 2022, which has a file size of 22,384 bites, and is herein incorporated by reference in its entirety.

TECHNICAL FIELD

The present technology relates to peptides that bind to the growth hormone receptor (GhR), to peptides that bind to the GhR and have antagonistic activity, and to compositions comprising such peptides.

BACKGROUND INFORMATION

Growth hormone (Growth Hormone; GH or Gh) is a hormone that is essential for growth and is secreted by growth hormone-secreting cells in the anterior pituitary gland. Growth hormone is known to have effects on various tissue, including growth, such as the elongation of bones and muscle growth, and metabolism, such as glycogenolysis in the liver. Growth hormone is secreted into the bloodstream when produced in the pituitary gland and binds to the growth hormone receptor (GhR) that is expressed on various cell surfaces, such as the liver, muscle tissue, and bone tissue. Binding of GH to the GhR induces the production of insulin-like growth factor-1 (IGF-1) in certain cells, particularly in liver cells. IGF-1 then stimulates the growth of the whole body and exhibits a growth promoting effect on somatic cells.

As an example of a compound that binds to the GhR, a growth hormone variant compound that binds to the human GhR is described in JP 2016-511275 A (Translation of PCT Application) incorporated herein by reference, and furthermore, a method for producing a subject's response to a drug capable of binding to the human GhR is described in JP 2006-525785 A (Translation of PCT Application) incorporated herein by reference. Thus, various drugs having avidity for GhR are being examined.

Using a peptide that binds to GhR (GhR-binding peptide), the distribution and amount of GhR expression may be confirmed, for example, by measuring the binding of a fluorescent or isotope-labeled peptide to GhR. Furthermore, the affinity of a ligand for the GhR, or for different species GhRs may be determined through the use of GhR-binding peptides. Additionally, it is possible to use a GhR-binding peptide to target and transport compounds having pharmacological actions to the GhR, such as isotopes, low molecular weight compounds, peptides, proteins, antibodies, and nucleic acids.

Therefore, novel GhR-binding peptides and compositions comprising the GhR-binding peptide are both useful and desired.

SUMMARY OF TECHNOLOGY

An aspect of the present technology is to provide a peptide that binds to GhR, in particular to human GhR, and a composition comprising such GhR-binding peptide.

In some embodiments, the peptide of the present technology is an isolated peptide.

In some embodiments, the peptide of the present technology is a purified peptide.

In some embodiments, the peptide of the present technology has the following amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$ (SEQ ID NO: 1), wherein:
  $X_1$ is an amino acid having an aromatic ring or a substitution thereof;
  $X_2$ is an N-alkyl amino acid or a modification thereof;
  $X_3$ and $X_4$ are each independently a branched-chain amino acid;
  $X_5$ is any amino acid;
  $X_6$ is N (asparagine);
  $X_7$ is W (tryptophan) or a substitution thereof;
  $X_8$ is an amino acid having in the side chain an aromatic ring or a substitution thereof;
  $X_9$ is K (lysine) or a substitution thereof, or is R (arginine) or a substitution thereof;
  $X_{10}$ is an amino acid having in the side chain an aromatic ring or a substitution thereof;
  $X_{11}$ is A (alanine) or a substitution thereof, or is K (lysine) or a substitution thereof;
  $X_{12}$ is any amino acid; and
  $X_{13}$ is C (cysteine); and
  wherein the peptide or the salt thereof comprises none, one, two or three substitution, deletion, addition, or insertion, and wherein the peptide or the salt thereof has avidity for GhR.

In some implementations of these embodiments, $X_2$ is N-methyllysine or a modification thereof; $X_3$ and $X_4$ are each V (valine); $X_5$ is S (serine); $X_7$ is substituted W (tryptophan); $X_8$ is F (phenylalanine) or a substitution thereof or Y (tyrosine) or a substitution thereof; $X_9$ is K (lysine) or a substitution thereof or R (arginine) or a substitution thereof; $X_{10}$ is substituted W (tryptophan); $X_{11}$ is A (alanine) or a substitution thereof or K (lysine) or a substitution thereof; and $X_{12}$ is V (valine).

In some implementations of these embodiments, $X_2$ is N-methyllysine or a modification thereof; $X_7$ is 1-(carboxymethyl)-L-tryptophan (W1aa), and the amino acid residues of $X_2$ and $X_7$ are bound.

In some implementations of these embodiments, $X_2$ is N-methyllysine in which an albumin binder is bound. The albumin binder may be directly bound to N-methyllysine or may be bound through another amino acid residue or a linking group.

In some implementations of these embodiments, the albumin binder is any one of 4IphpCO, Biph4pCO, PhPeCO, PhpCO, cC14COO, and 4MePhpCO.

In some implementations of these embodiments, $X_1$ is Y, 4Py, or F4COO; $X_8$ is Y or F4COO; $X_9$ is K, KCOpipzaa, Hgn, Ahp, or Har; $X_{10}$ is W5H; and $X_{11}$ is Aib or A4pipaa.

In some embodiments, the peptide or the salt of the present technology has an amino acid sequence represented by F4COO-MeK-V-V-S-N-W1aa-F4COO-K-W5H-Aib-V-C (SEQ ID NO: 10) or has an amino acid sequence in which one, two or three amino acid residues from SEQ ID NO: 10 have been substituted, deleted, added, or inserted, in which the second and seventh amino acid residues in SEQ ID NO: 10 are bound, and the peptide or the salt thereof has avidity for hGhR.

In some embodiments, the peptide or the salt of the present technology has an amino acid sequence represented by Y-MeK-V-V-S-N-W5OMe-F4COO-K-W5H-A4pipaa-V-C (SEQ ID NO: 30) or has an amino acid sequence in which one, two or three amino acid residues from SEQ ID NO: 30 have been substituted, deleted, added, or inserted, in which an albumin binder is bound to MeK, which is the second amino acid residue of SEQ ID NO: 30, and the peptide or the salt thereof has avidity for hGhR.

In some embodiments, the albumin binder is any one of 4IphpCO, Biph4pCO, PhPeCO, PhpCO, cC14COO, and 4MePhpCO. In some embodiments, the albumin binder is 4IphpCO. In some embodiments, the albumin binder is Biph4pCO. In some embodiments, the albumin binder is PhPeCO. In some embodiments, the albumin binder is PhpCO. In some embodiments, the albumin binder is cC14COO. In some embodiments, the albumin binder is Biph4pCO.

In some embodiments, the peptide or the salt of the present technology is a cyclic peptide or a salt of a cyclic peptide.

In some embodiments, the peptide or the salt of the present technology has a cyclic structure in which a chloroacetylated first amino acid residue and a cysteine residue are bound.

In some embodiments, the peptide or the salt of the present technology has an amino acid sequence selected from SEQ ID NOs: 2 to 9, 11 to 29 and 31.

In some embodiments, the peptide or the salt of the present technology has an amino acid sequence selected from SEQ ID NOs: 2 to 9, 11 to 29 and 31 and further comprises a liker at the C-terminus.

In some implementations of this embodiment, the linker has an amino acid sequence selected from Lysine and SEQ ID NO: 33.

In some embodiments, the peptide or the salt of the present technology has hGhR antagonistic activity.

In some embodiments, the peptide or the salt of the present technology includes any combination described herein and any peptide or salt thereof described herein.

In some embodiments, the present technology relates to a pharmaceutical composition.

In some embodiments, the pharmaceutical composition of the present technology comprises any peptide or salt thereof described herein, and a pharmaceutically acceptable carrier, excipient, or additive.

In some embodiments, the pharmaceutical composition of the present technology has hGhR antagonistic activity. Therefore, this pharmaceutical composition is effective for the treatment of diseases associated with human growth hormone hypersecretion (for example, acromegaly or gigantism) and may be used as a pharmaceutical composition for the treatment of these diseases.

In some embodiments, the present technology relates to a treatment method for a disease associated with human growth hormone hypersecretion.

In some embodiments, the treatment method of the present technology is for treatment of a disease associated with human growth hormone hypersecretion, the method including a step for administering the pharmaceutical composition described above (or a peptide or a salt thereof described above) to a patient having a disease associated with human growth hormone hypersecretion.

In some embodiments, the disease associated with human growth hormone hypersecretion is acromegaly or gigantism.

Since the peptide of the present technology has the ability to bind to the GhR, it is possible for the peptide to target and transport compounds having pharmacological actions to the GhR, such as isotopes, low molecular weight compounds, peptides, proteins, antibodies, and nucleic acids.

Other aspects and features of the present disclosure will become apparent to those ordinarily skilled in the art upon review of the following description of specific embodiments in conjunction with the accompanying drawings.

BRIEF DESCRIPTION OF THE DRAWINGS

All features of embodiments which are described in this disclosure are not mutually exclusive and can be combined with one another. For example, elements of one embodiment can be utilized in the other embodiments without further mention. A detailed description of specific embodiments is provided herein below with reference to the accompanying drawings in which:

FIG. 1 is a diagram outlining a sequence example of a peptide according to one embodiment of the present technology.

FIG. 2 is a diagram outlining a sequence example of linker sites in a peptide according to one embodiment of the present technology.

DETAILED DESCRIPTION

It should be understood that both the general descriptions and the detailed description below are merely illustrative and descriptive and do not limit the present technology of the present application. In the present specification, the use of the singular form includes the plural form unless otherwise specified. In the present specification, the use of "or (or)" means "and/or (and/or)" unless otherwise stated. Furthermore, terms such as "element" or "component" encompass both an element and a component including one unit and an element and a component including two or more subunits unless when otherwise specified.

The headings used in the present specification are for structural purposes only and must not be construed as limiting the subject matter described. All of the documents or parts of the documents cited in the present application including but not limited to patents, patent applications, articles, books, and papers are expressly incorporated by reference in part or entirety from among the documents discussed in the present specification.

The recitation herein of numerical ranges by endpoints is intended to include all numbers subsumed within that range (e.g., a recitation of 1 to 5 includes 1, 1.5, 2, 2.75, 3, 3.80, 4, 4.32, and 5).

The term "about" is used herein explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. For example, the term "about" in the context of a given value or range refers to a value or range that is within 20%, preferably within 15%, more preferably within 10%, more preferably within 9%, more preferably within 8%, more preferably within 7%, more preferably within 6%, and more preferably within 5% of the given value or range.

As used herein, the term "comprise" is used in its non-limiting sense to mean that items following the word are included, but items not specifically mentioned are not excluded.

Unless special definitions are given, the terminology used in relation to analytical chemistry, synthetic organic chemistry, and medical chemistry and pharmaceutical chemistry described in the present specification, as well as their procedures and techniques, are well known and commonly used in the field of the present art. Standard techniques may be used for chemical synthesis and chemical analysis. Those defined from among such techniques and procedures can be found in, for example, "K. J. Jensen, P. T. Shelton, S. L. Pedersen, Peptide Synthesis and Applications, 2nd Edition, Springer, 2013" and the like, and these are incorporated into the present specification by reference for all purposes. All patents, applications, published applications, and other publications, and other data referred to throughout the entire disclosure, when permitted, are incorporated into the present specification by reference.

Abbreviations

Unless otherwise stated in the present specification, the following abbreviations are used according to the following meanings:
BiPh4pCO: 4-([1,1'-biphenyl]-4-yl) butanoic acid (CAS No.: 6057-60-9);
Boc: Tert-butoxycarbonyl tert-butoxycarbonyl;
cC12COO: Tetradecanedioic acid (CAS No.: 821-38-5);
cC13COO: Pentadecanedioic acid (CAS No.: 1460-18-0);
cC14COO: Hexadecanedioic acid (CAS No.: 505-54-4);
cC15COO: Heptadecanedioic acid (CAS No.: 2424-90-0);
ClAc: Chloroacetyl;
DCM: Dichloromethane;
DIC: N,N'-Diisopropylcarbodiimide;
DMSO: Dimethylsulfoxide;
DMF: Dimethylformamide;
DIPEA or DIEA: N,N-Diisopropylethylamine;
DODT: 6-Dioxa-1,8-octanedithiol;
E_cC14COO: N-(15-Carboxy-1-oxopentadecyl)-L-glutamic acid (CAS No.: 1472005-57-4);
Fmoc: 9-Fluorenylmethyloxycarbonyl;
g: Gram (unit);
HOSu: N-Hydroxysuccinimide N-hydroxysuccinimide;
HPLC: High-performance liquid chromatography;
ivDde: 1-(4,4-Dimethyl-2,6-dioxocyclohex-1-ylidene)-3-methylbutyl 1-(4,4-dimethyl-2,6-dioxocyclohex-1-ylidene)-3-methylbutyl;
LC-MS or LC/MS: Liquid chromatography-mass spectrometer;
MeCN: Acetonitrile;
mL: Milliliter (unit);
M: Molar (unit);
µL: Microliter (unit);
mM: Millimolar (unit);
Micromolar (unit);
mg: Milligram (unit);
mm: Millimeter (unit);
nm: Nanometer (unit);
nM: Nanomolar (unit);
Oxyma pure: Ethyl cyano(hydroxyimino)acetate;
PhpCO: 4-phenylbutanoic acid (CAS No.: 1821-12-1);
PhPeCO: 6-phenylhexanoic acid (CAS No.: 5581-75-9);
qPCR: Quantitative PCR;
rpm: Revolutions per minute (unit);
tBu: tert-Butyl;
TFA: Trifluoroacetic acid;
TIS: Triisopropylsilane;
Trt or Tr: Trityl group;
4IPhpCO: 4-(p-Iodophenyl) butyric acid (CAS No.: 27913-58-2, Merck);
4MePhpCO: 4-(p-tolyl) butanoic acid (CAS No.: 4521-22-6).

Abbreviations (Unnatural Amino Acids)

W5OMe: 5-Methoxy-L-tryptophan (CAS N.: 25197-96-0);
F4COO: 4-Carboxy-L-Phenylalanine (CAS No.: 126109-42-0);
W5H: 5-Hydroxy-L-Tryptophan (CAS No.: 2382808-45-7);
Aib: Alpha-Methyl Alanine (CAS No.: 62-57-7);
ds: D-Serine (CAS No.: 312-84-5);
W1aa: 1-(Carboxymethyl)-L-Tryptophan (CAS No.: 773823-50-0);
A4pipaa: 4-Amino-1-(carboxymethyl) piperidine-4-carboxylic acid (Kishida Chemical Inc.);
Hgn: (S)-2,6-diamino-6-oxohexanoic acid (CAS No.: 1263046-43-0);
Har: N6-carbamimidoyl-L-lysine (CAS No.: 214852-52-5);
KCOpipzaa: N6-(4-(carboxymethyl) piperazine-1-carbonyl)-L-lysine (Kishida Chemical Inc.);
PEG2Ac: 2-(2-(2-aminoethoxy)ethoxy)acetic acid (CAS No.: 134978-97-5);
4Py: 4-pyridyl-L-alanine (CAS No.: 169555-95-7);
W7N: (S)-2-amino-3-(1H-pyrrolo[2,3-b]pyridin-3-yl) propanoic acid (CAS No.: 737007-45-3);
Ahp: (s)-2-aminoheptanic acid (CAS No.: 44902-02-5);
Me: N-Methyl;
MeK: N-Methyl-L-Lysine (CAS No.: 7431-89-2);
3Py6COO: 5-[(2S)-2-amino-2-carboxyethyl]pyridine-2-carboxylic acid;

Peptide

In one embodiment, the peptide of the present technology has the acid sequence: X1-X2-X3-X4-X5-X6-X7-X8-X9-X10-X11-X12-X13, as set forth in SEQ ID NO: 1, wherein:
X1 is an amino acid having an aromatic ring or a substitution thereof in the side chain;
X2 is an N-alkyl amino acid or a modification thereof;
X3 and X4 are each a branched-chain amino acid;
X5 is any amino acid;
X6 is N (asparagine),
X7 is W (tryptophan) or a substitution thereof;
X8 is an amino acid having an aromatic ring or a substitution thereof in the side chain;
X9 is K (lysine) or a substitution thereof, or is R (arginine) or a substitution thereof;
X10 is an amino acid having an aromatic ring or a substitution thereof in the side chain;
X11 is A (alanine) or a substitution thereof, or is K (lysine) or a substitution thereof;
X12 is any amino acid, and
X13 is C (cysteine); and
wherein the peptide comprises none, one, two or three amino acid substitution, deletion, addition or insertion. In some implementations of this embodiment, the peptide of the present technology has avidity for GhR.

In some embodiments, the peptide of the present technology having an amino acid sequence as represented in SEQ ID NO: 1 comprises a substitution, addition, deletion, or insertion. The number of amino acids substituted, deleted, added, and/or inserted of the amino acids may be one or more and three or less, and the lower limit thereof is one. The upper limit thereof is two, and the minimum is one. In some embodiments, the amino acid substitution is a conservative amino acid substitution. In some further implementations, the one to three such amino acid substitutions occurs at positions selected from X1, X2, X7, X8, X9, X10, and X11 in SEQ ID NO: 1.

As used herein, the expression "conservative amino acid substitution" refers to a substitution of functionally equivalent or similar amino acids. A conservative amino acid substitution in a peptide brings about a static change to the amino acid sequence of the peptide. For example, one or two or more amino acids having similar polarity act functionally equivalent to each other and bring about a static change in the amino acid sequence of the peptide. In general, a substitution within a certain group may be considered conservative regarding structure and function. However, as is clear to a person having ordinary skill in the art, the role played by a defined amino acid residue may be determined by its implication in the three-dimensional structure of the molecule containing the amino acid. For example, a cysteine residue may be an oxidized-type (disulfide) foam having a lower polarity than that of a reduced-type (thiol) foam. The long aliphatic part of the arginine side chain may constitute structurally and functionally important features. Furthermore, the side chain (tryptophan, tyrosine, phenylalanine) including an aromatic ring may contribute to ion-aromatic interaction or cation-pi interaction. In such a case, even if the amino acids having these side chains are substituted for amino acids belonging to the acidic or non-polar groups, they may be structurally and functionally conservative. There is a possibility that residues such as proline, glycine, cysteine (disulfide foam) have a direct effect on the three-dimensional structure of the main chain and often may not be substituted without structural distortion.

Conservative amino acid substitution, as shown below, includes specific substitution based on the similarity of side chains (for example, substitutions are described in Lehninger, Biochemistry, Revised 2nd Edition, published in 1975, pp. 73 to 75: L. Lehninger, Biochemistry, 2nd edition, pp. 73 to 75, Worth Publisher, New York (1975)), incorporated herein by reference, and typical substitution.

Further to conservative amino acid substitution, for example, in the group obtained by dividing natural amino acids such as the following based on the properties of their common side chains, substitution for an amino acid belonging to the same group as the group to which a certain amino acid belongs is preferable.

Hydrophobic (also referred to as non-polar) amino acids: Amino acids that exhibit hydrophobicity (non-polarity), including alanine (also referred to as "Ala" or simply "A"), glycine (also referred to as "Gly" or simply "G"), valine (also referred to as "Val" or simply "V"), leucine (also referred to as "Leu" or simply "L"), isoleucine (also referred to as "Ile" or simply "I"), proline (also referred to as "Pro" or simply "P"), phenylalanine (also referred to as "Phe" or simply "F"), tryptophan (also referred to as "Trp" or simply "W"), tyrosine (also referred to as "Tyr" or simply "Y"), and methionine (also referred to as "Met" or simply "M").

Hydrophobic amino acids may be further divided into the following groups:

Aliphatic amino acids: Amino acids having a fatty acid or hydrogen in the side chain, including Ala, Gly, Val, Ile, and Leu.

Aliphatic/branched-chain amino acids: Amino acids having a branched fatty acid in the side chain, including Val, Ile, and Leu.

Aromatic amino acids: Amino acids having an aromatic ring in the side chain, including Trp, Tyr, and Phe.

Hydrophilic (also referred to as polar) amino acids: Amino acids that exhibit hydrophilicity (polarity), including serine (also referred to as "Ser" or simply "S"), threonine (also referred to as "Thr" or simply "T"), cysteine (also referred to as "Cys" or simply "C"), asparagine (also referred to as "Asn" or simply "N"), glutamine (also referred to as "Gln" or simply "Q"), aspartic acid (also referred to as "Asp" or simply "D"), glutamic acid (also referred to as "Glu" or simply "E"), lysine (also referred to as lysine. Also referred to as "Lys" or simply "K"), arginine (also referred to as "Arg" or simply "R"), and histidine (also referred to as "His" or "H").

Hydrophilic amino acids may be further divided into the following groups:

Acidic amino acids: Amino acids whose side chains exhibit acidity, including Asp and Glu.

Basic amino acids: Amino acids whose side chains exhibit basicity, including Lys, Arg, and His.

Neutral amino acids: Amino acids whose side chains exhibit neutrality, including Ser, Thr, Asn, Gln, and Cys.

Furthermore, Gly and Pro may be divided into "amino acids that affect the direction of the main chain", and amino acids, Cys, and Met which contain sulfur molecules in the side chains may be divided into "sulfur-containing amino acids".

As used herein, the expression "amino acid" includes not only natural amino acids but also unnatural amino acids. Unnatural amino acids include, for example, N-alkyl amino acids in which a natural amino acid described above is N-alkylated; and those modified with lower alkyl groups (for example, of C1 to C5, preferably C1 to C3, and more preferably C1) in which the nitrogen forming a peptide bond is branched or not branched. Among the N-alkyl amino acids, N-ethyl amino acid, N-butyl amino acid, or N-methyl amino acid is preferable, and N-methyl amino acid is more preferable. Furthermore, unnatural amino acids also include D-type amino acids (also referred to as D-amino acids), chemically modified amino acids such as β-amino acids, γ-amino acids, amino acid variants, amino acid derivatives, or the like; amino acids that are not constituent materials for proteins in vivo, such as norleucine, ornithine, or the like; or the like. Also included are amino acids to which a functional group is further added to the side chain of a natural amino acid or substituted for another functional group (for example, an amino acid having a substitution or an addition in a part such as an arylene group, an alkylene group, or the like of the side chain; an amino acid wherein the arylene group or the alkyl group of the side chain has an increased C-number; an amino acid having a substitution in the aromatic ring of the side chain; a heterocyclic or condensed cyclic amino acid; or the like).

By adding or substituting a structure such as a functional group in the side chain of a natural amino acid, a property different from that of the natural amino acid may be imparted. For example, A4p is an amino acid having a piperidyl group in the side chain of alanine, but by adding the piperidyl group, it exhibits a property of a polar amino acid having basicity, unlike alanine which belongs to the non-polar amino acid group. Namely, the group described above, obtained by dividing natural amino acids based on the properties of their common side chains, may include unnatural amino acids having the same side chain property. For example, N-methyllysine (MeK), which is an amino acid in which the nitrogen atom in the main chain of lysine belonging to a basic amino acid is methylated, is an unnatural amino acid, but it may be classified as a basic amino acid because it exhibits basicity. Thus, an unnatural amino acid exhibiting the same side chain property as that of a certain amino acid may also be included as the subject of a conservative amino acid substitution.

In a non-limiting manner, unnatural amino acids include, but are not limited to N-methyl amino acids, W5OMe, F4COO, W5H, Aib, ds, W1aa, A4pipaa, Hgn, Har, KCOpipzaa, 4Py, W7N, Ahp, and the like. For example, W5OMe, F4COO, W5H, Aib, W1aa, W7N, and Ahp may be divided into hydrophobic amino acids; 4Py, A4pipaa, ds, Har, and KCOpipzaa may be divided into hydrophilic amino acids; furthermore, Ahp and Aib may be divided into aliphatic amino acids; KCOpipzaa may be divided into an acidic amino acid; Har, 4Py, and A4pipaa may be divided into basic amino acids; Hgn and ds may be divided into neutral amino acids; and W5OMe, W5H, W1aa, F4COO, and W7N may be divided into aromatic amino acids. Note that D-amino acids such as ds may be classified as D-amino acids, but they may also be classified according to the properties of their side chains, and N-methyl amino acids may be classified as N-alkyl amino acids and may also be classified according to the property of the side chain of the original amino acid that has not undergone N-methylation.

Among amino acids having an aromatic ring or a substitution thereof in the side chain, an amino acid having an unsubstituted aromatic ring in the side chain is an amino acid having an aromatic ring in the side chain and includes a natural amino acid belonging to an aromatic amino acid; an unnatural amino acid such as an N-acetylated aromatic amino acid; or an amino acid having an aromatic ring added or substituted in the side chain of a natural amino acid. Furthermore, an amino acid having a substituted aromatic ring in the side chain is an amino acid having an aromatic ring in the side chain and includes an amino acid in which some molecules of the aromatic ring in a natural amino acid belonging to an aromatic amino acid or an unnatural amino acid, such as an N-acetylated aromatic amino acid, have a ring substituted for another molecule or functional group or a heterocyclic ring, or an amino acid wherein such has a condensed cyclic ring. For example, also included is an amino acid having a substitution in the side chain hydroxy group of Tyr; an amino acid having a substituent in the benzene ring of Phe; or an amino acid having a ring containing a heteroatom in the side chain indole ring of Trp; an amino acid having a substituent; as well as an amino acid having a functional group added to these.

Furthermore, among W or a substitution thereof, unsubstituted W is tryptophan, which is a natural amino acid, and substituted W includes a derivative amino acid of W having a heteroatom in the indole ring of W in the side chain; a derivative amino acid of W in which the hydrogen contained by NH in the indole ring is substituted; a derivative amino acid of W having a substituent in the benzene ring; or the like.

Among K or a substitution thereof, unsubstituted K is lysine, which is a natural amino acid, and substituted K includes a derivative amino acid of K having a substituent in the amino group of K in the side chain (including a derivative in which an amino group is substituted for hydrogen); a derivative amino acid of K in which an aminobutyl group of K in the side chain is substituted for an aminoalkyl group having a branched-chain or straight-chain structure; also a derivative amino acid of K in which the alkyl group has a substituent; or the like.

Among R or a substitution thereof, unsubstituted R is arginine which is a natural amino acid, and substituted R includes a derivative amino acid of R having a substituent in a guanidino group of R in the side chain (including a derivative in which the guanidino group is substituted for hydrogen); a derivative amino acid of R in which a pentyl group of R in the side chain is substituted for an alkyl group having a branched-chain or a straight-chain structure; also a derivative amino acid of R in which the alkyl group has a substituent; or the like.

Among A or a substitution thereof, unsubstituted A is alanine, which is a natural amino acid, and substituted A includes a derivative amino acid of A in which the α-hydrogen of A is substituted; or the like.

Among Y or a substitution thereof, unsubstituted Y is tyrosine which is a natural amino acid, and substituted Y includes a derivative amino acid of Y in which the hydroxyl group of phenol of Y in the side chain is substituted; a derivative amino acid of Y having a heterocyclic ring, or a derivative amino acid of Y having a condensed polycyclic structure; or the like.

Among F or a substitution thereof, unsubstituted F is phenylalanine which is a natural amino acid, and substituted F includes an amino acid having a substituent in the benzene ring of phenylalanine in the side chain; a derivative amino acid of F having a heterocyclic ring, or a derivative amino acid of F having a condensed polycyclic structure; or the like.

Furthermore, the N-alkyl amino acid or a modification thereof is the amino acid in which a functional group or an amino acid, a compound, or the like may be added to the side chain of the N-alkyl amino acid. As for examples of the N-alkyl amino acid or a modification thereof, the N-alkyl amino acid is N-alkyllysine or N-methyllysine. Another example of the modified N-alkyl amino acid is N-methyllysine in which an albumin binder is bound or N-methyllysine in which one or more of any amino acid is bound. Another example of the modified N-alkyl amino acid is the N-methylly sine in which an albumin binder is bound to the amino group in the side chain of N-methyllysine, or the N-methyllysine in which one or two of glycine, N-methylglycine, or proline are bound.

The foregoing options for X1 to X11 of SEQ ID NO: 1 may be selected in any combination.

In one aspect, X1 of SEQ ID NO: 1 is Y, 4Py, or F4COO.

In one aspect, X2 of SEQ ID NO: 1 is N-methyllysine or a modification thereof. In a further aspect, X2 of SEQ ID NO: 1 is N-methyllysine or modified N-methyllysine.

In one aspect, X3 and X4 of SEQ ID NO: 1 are each V.

In one aspect, X5 of SEQ ID NO: 1 is S.

In one aspect, X6 of SEQ ID NO: 1 is N.

In one aspect, X7 of SEQ ID NO: 1 is substituted W. In a further aspect, X7 of SEQ ID NO: 1 is W5OMe, W7N, or W1aa.

In one aspect, X8 of SEQ ID NO: 1 is substituted F or substituted Y. In a further aspect, X8 of SEQ ID NO: 1 is Y or F4COO.

In one aspect, X9 of SEQ ID NO: 1 is substituted K or R. In a further aspect, X9 of SEQ ID NO: 1 is K, KCOpipzaa, Hgn, Ahp, or Har.

In one aspect, X10 of SEQ ID NO: 1 is substituted W. In a further aspect, X10 of SEQ ID NO: 1 is W5H.

In one aspect, X11 of SEQ ID NO: 1 is substituted A or K. in a further aspect, X11 of SEQ ID NO: 1 is Aib or A4pipaa.

In one aspect, X12 of SEQ ID NO: 1 is V.

In one aspect, X13 of SEQ ID NO: 1 is C.

The foregoing options of one aspect for X1 to X13 of SEQ ID NO: 1 may be selected in any combination. In the present specification, the expressions "in a non-limiting manner" and "in one aspect" may be used interchangeably.

In one embodiment, the peptide of the present technology is a cyclic peptide. As used herein, the expression "cyclic peptide" refers to a peptide in which two amino acids are bound and the entirety or a part thereof are cyclic. This peptide also includes an amino acid in the peptide forming a cross-linked structure; forming a cyclic structure by lactam ring formation or a macrocyclization reaction; having a lasso peptide-like structure; and the like. That is, a part of the cyclic peptide may form a cyclic structure, or it may have a straight-chain part.

In some instances, some peptides exhibit poor metabolic stability in vivo, and some peptides are large in size, making it difficult for them to penetrate cell membranes. A method for cyclizing a peptide has been adopted in light of such problems. It has been suggested that when a peptide is cyclized, protease resistance is improved, metabolic stability is improved, and restrictions are also added to conformational change, so that rigidity is increased and membrane permeability and affinity for the target protein is improved.

In one aspect, the peptide of the present technology has a cyclic structure in which a chloroacetylated amino acid and a cysteine residue present in the peptide are bound. In one aspect, the peptide has a cyclic structure in which an N-terminal amino acid (first amino acid residue) and a cysteine residue present in the peptide are bound. In one aspect, the peptide has a cyclic structure in which an N-terminal amino acid (first amino acid residue) and the thirteenth cysteine residue present in the peptide are bound. In one aspect, the peptide has a cyclic structure in which a chloroacetylated N-terminal amino acid (first amino acid residue) and the thirteenth cysteine residue present in the peptide are bound. "Chloroacetylation" may be "halogen acetylation" using another halogen. Furthermore, "acetylation" may be "acylation" using an acyl group other than an acetyl group.

In some embodiments, the peptide of the present technology has an amino acid sequence according to any one of SEQ ID NOs: 2 to 31.

In some embodiments, the peptide of the present technology consists of an amino acid sequence according to any one of SEQ ID NOs: 2 to 31.

In some embodiments, the peptide of the present technology is a cyclic peptide having an amino acid sequence according to any one of SEQ ID NOs: 2 to 31.

In some embodiments, the peptide of the present technology is a cyclic peptide consisting of an amino acid sequence according to any one of SEQ ID NOs: 2 to 31.

The number of amide bonds (the number and length of amino acids) of the peptide and the peptide site comprised in the peptide of the present technology is not particularly limited. It is preferable that the total amino acid residue (referring to the number of amino acid residues comprised in the peptide forming the cyclic structure, and when the amino acid residues are further added in a linker form from the cyclic peptide, they are not included) is within 20 residues. In some implementations, the number of amino acids is 6 or more, 7 or more, 8 or more, 9 or more, 10 or more, 11 or more. In some other implementations, the number of amino acids is 19 or less, 18 or less, 17 or less, 16 or less, 15 or less, 14 or less, 13 or less, or 12 or less.

In some embodiments, the peptide of the present technology comprises between 6 amino acids and 19 amino acids. In some embodiments, the peptide of the present technology comprises between about 6 amino acids and 17 amino acids. In some embodiments, the peptide of the present technology comprises between about 6 amino acids and 15 amino acids. In some embodiments, the peptide of the present technology comprises between about 6 amino acids and 14 amino acids. In some embodiments, the peptide of the present technology comprises between about 6 amino acids and 13 amino acids. In some embodiments, the peptide of the present technology comprises between about 6 amino acids and 12 amino acids.

In some embodiments, the peptide of the present technology comprises between 8 amino acids and 19 amino acids. In some embodiments, the peptide of the present technology comprises between about 8 amino acids and 17 amino acids. In some embodiments, the peptide of the present technology comprises between about 8 amino acids and 15 amino acids. In some embodiments, the peptide of the present technology comprises between about 8 amino acids and 14 amino acids. In some embodiments, the peptide of the present technology comprises between about 8 amino acids and 13 amino acids. In some embodiments, the peptide of the present technology comprises between about 8 amino acids and 12 amino acids.

In some embodiments, the peptide of the present technology comprises between 10 amino acids and 19 amino acids. In some embodiments, the peptide of the present technology comprises between about 10 amino acids and 17 amino acids. In some embodiments, the peptide of the present technology comprises between about 10 amino acids and 15 amino acids. In some embodiments, the peptide of the present technology comprises between about 10 amino acids and 14 amino acids. In some embodiments, the peptide of the present technology comprises between about 10 amino acids and 13 amino acids. In some embodiments, the peptide of the present technology comprises between about 10 amino acids and 12 amino acids.

Moreover, a linker may be further added from the cyclic peptide. Examples of the linker include the foregoing amino acid linker (peptide linker), a chemical linker, a fatty acid linker, a nucleic acid linker, a sugar chain linker, or the like, or it may be a complex, for example, a chemical linker, a peptide linker, or the like. Examples of the chemical linker include a PEG (polyethylene glycol) linker. For example, the PEG linker may comprise between 1 to 24 ethylene glycol units. Furthermore, the linker may be a fatty acid linker containing a divalent chemical moiety derived from a fatty acid. The linker includes at least one amino acid, and, for example, a glycine-rich peptide such as a peptide having a sequence [Gly-Gly-Gly-Gly-Ser] n (in the formula, n is 1, 2, 3, 4, 5, or 6) such as that according to U.S. Pat. No. 7,271,149, incorporated by reference herein, or a serine-rich peptide linker according to U.S. Pat. No. 5,525,491, incorporated by reference herein, may be used. In a non-limiting manner, there are some cases where a physical property (for example, solubility) of the peptide may be changed by the addition of a linker. In one aspect, the amino acid linker includes Lysine Glycine, or an amino acid sequence according to SEQ ID NO: 32 or 33.

The linker may be added at any position. For example, it may be bound to Cys positioned on the N-terminal side or may be bound to an amino acid comprised in the cyclic peptide. In some instances, it is bound to Cys positioned on the N-terminal side.

GhR-Binding Peptide and Peptide Having GhR Antagonistic Activity

In some embodiments, the peptide of the present technology binds to GhR. In some implementations of these embodiments, the peptide has GhR antagonistic activity. In some instances, the peptide binds to human GhR (hGhR) and has hGhR antagonistic activity.

As used herein, the term "GhR" refers to any form of GhR and a variant thereof for retaining at least a part of the activity of GhR. The GhR includes all the native sequences of GhR in mammals such as, for example, humans, dogs, cats, horses, and cows, unless otherwise specifically described as human GhR (hGhR). One exemplification of GhR is hGhR (Gene ID: 2690), which is human GhR, having two disulfide crosslinks, a molecular weight of 22 kDa, and is a protein having an amino acid length of 191.

As used herein, the expression "binds to GhR" indicates having the activity of binding to GhR. Binding to GhR may be measured by any method for measuring known intermolecular binding. In a non-limiting manner, for example, this may be determined by competitive binding assays such as surface plasmon resonance (SPR) assays, scatter analysis and/or radioimmunoassays (RIA), enzyme immunoassays (EIA), and sandwich and competitive assays, and in any suitable manner which is known, including different variants of the examples given that are known in the technical field.

As used herein, the expression "GhR antagonistic activity" indicates the biological activity of GhR and/or activities that inhibit (one or a plurality of) downstream pathways mediated by GhR signaling Peptides having GhR antagonistic activity include peptides capable of blocking, antagonizing, and suppressing or reducing (to any degree, including a remarkable degree) the biological activity of GhR including downstream pathways mediated by GhR signaling, and, for example, GH interaction and/or induction of a cellular response to GH, and the like. For the purpose of the present technology, it will be explicitly understood that the phrase "peptide having GHR antagonistic activity" encompasses all of the previously defined terms, titles, and functional states and characteristics whereby the GHR itself, a GHR biological activity (including but not limited to its ability to mediate any aspect of insulin-like growth factor-1 (IGF-1) expression), or the outcome of the biological activity, are substantially nullified, decreased, or neutralized in any meaningful degree. In one aspect, a peptide having GhR antagonistic activity binds to the GhR to affect and/or prevent interaction between the growth hormone and the GhR. In some embodiments, a peptide having GhR antagonistic activity binds to GhR to affect and/or prevent GhR dimerization.

In some embodiments, the peptide of the present technology has a bicyclic structure. As used herein, the expression "bicyclic structure" refers to a peptide having two or more cyclic structures. As one example, the peptide having a bicyclic structure is a cyclic peptide having a cyclic structure in which a chloroacetylated amino acid and a cysteine residue present in the peptide are bound, and wherein the cyclic peptide also has a cross-linked structure in the ring. In one aspect, the peptide having a bicyclic structure is a peptide in which the amino acid residue of X2 in SEQ ID NO: 1 is N-methyllysine and the amino acid residue of X7 is W1aa, wherein the peptide has a cyclic structure in which a chloroacetylated X1 amino acid residue and a cysteine residue of X13 are bound, and also has a structure in which the X2 amino acid residue and the X7 amino acid residue are bound. Furthermore, in one aspect, one or more amino acids may be present between the X2 amino acid residue and the X7 amino acid residue. For example, the amino group of the side chain of N-methyllysine, which is the X2 amino acid residue, may be bound to the carboxylic acid of the side chain of W1aa, which is an X6 amino acid residue, to form a bicyclic structure, and furthermore, the amino group of the side chain of N-methyllysine and the carboxylic acid of the side chain of W1aa, which is the X6 amino acid residue, may be bound through glycine, N-methylglycine, or proline.

In some embodiments, the peptide of the present technology comprises an albumin binder. As used herein, the expression "albumin binder" refers to a compound that does not covalently bind to human serum albumin. Binding to human serum albumin may be measured by a known method for measuring avidity, such as the foregoing Surface Plasmon Resonance (SPR). A typical albumin binder suitable for use in the present technology includes a fatty acid such as myristic acid or palmitic acid, a derivative thereof, or a diphenylcyclohexane derivative. In one aspect, the albumin binder is a compound comprising a straight-chain and branched lipophilic group having 12 to 40 carbon atoms and a distal acidic group. In one aspect, the albumin binder is any of 4IphpCO, cC14COO, BiPh4pCO, PhpCO, PhPeCO, and 4MePhpCO. Furthermore, in the present specification, the albumin binder may have a structure comprising one or a plurality of glutamic acids. In some instances, the albumin binder has a structure in which the albumin binder is bound to the N-terminal of the peptide in which one glutamic acid or 2 to 5 glutamic acids are bound.

In one aspect, the albumin binder may be bound to an amino acid present in the cyclic structure site of the peptide or may be further bound to a linker bound to the peptide. As one example, in the case of being bound to the amino acid residue of X2 in SEQ ID NO: 1, N-methyllysine, which is the amino acid residue of X2, and a compound that does not covalently bind to human serum albumin are bound through a structure having one or a plurality of glutamic acids. A preferable aspect is one in which one or two glutamic acids are bound to the side chain of the N-methylly sine, and the albumin binder is bound to the N-terminal thereof.

Furthermore, as one example, an amino acid linker having human serum albumin including a structure having one or a plurality of glutamic acids is bound to the peptide. A preferable aspect is one in which an amino acid linker having Lysine (K) or G-P-(ds)$_3$-K (SEQ ID NO: 33) is bound to Cys existing on the C-terminal side of the peptide, one or two glutamic acids are bound to the side chain of lysine of the amino acid linker, and the albumin binder is bound to the N-terminal thereof.

Payload-Bound PDC Aspect

In one embodiment, the present technology relates to a complex. This complex comprises any of the peptides described herein, a linker bound to the peptide, and a substance bound to this linker. Since the peptide is capable of binding to the GhR, it is possible for the complex to transport the substance to the GhR.

The substance may be any substance desired by a person having ordinary skill in the art as long as it is a substance the skilled person desires to be delivered to the GhR. Examples of the substance are not limited, but include the following:

A compound: Including low molecular weight compounds, middle molecular weight compounds, and examples include known low molecular weight drugs.

A peptide: May be a peptide that binds to a target in the body and exhibits some kind of effect, for example, a cyclic peptide.

An RI: May be any compound that can be labeled by a radioisotope, such as a low molecular weight or middle molecular weight compound or an antibody labeled by a radioisotope. Examples include compounds for PET scanning A protein: May be any protein that exhibits a useful function in the body, such as an antibody or an enzyme. Examples include enzymes used in enzyme replacement therapy.

A nucleic acid: Any substance having a base sequence, such as DNA and RNA. Examples include nucleic acid medicines.

A molecule used in a drug delivery system (DDS): May be a known molecule used in DDS, such as a liposome or a micelle. The DDS molecule may further comprise a compound therein such as a pharmaceutical.

Moreover, the DDS molecule may be a complex in which several of the examples given above are combined.

Peptide Production

The peptide of the present technology may be produced by, for example, any known method for producing a peptide, such as the following:

a chemical synthesis method such as a liquid phase method, a solid phase method, a hybrid method combining a liquid phase method and a solid phase method, or the like;

a genetic recombination method; or the like.

In some of the instances where the peptide of the present technology is produced by a chemical synthesis method, it can be said that the peptide of the present technology is a synthetic peptide.

In the solid phase method, for example, a hydroxy group of a resin having a hydroxy group and a carboxy group of a first amino acid (normally a C-terminal amino acid of a target peptide) in which an α-amino group is protected by a protecting group are subjected to an esterification reaction. For the esterification catalyst, a known dehydrating and condensing agent such as 1-mesitylenesulfonyl-3-nitro-1,2,4-triazole (MSNT), dicyclohexylcarbodiimide (DCC), and diisopropylcarbodiimide (DIC) may be used.

Next, the protecting group of the α-amino group of the first amino acid is removed, a second amino acid in which all functional groups except the carboxy group of the main chain are protected is added, and the carboxy group is activated, binding the first and second amino acids. Furthermore, the α-amino group of the second amino acid is deprotected, a third amino acid in which all functional groups except the carboxy group of the main chain are protected is added, the carboxy group is activated, binding the second and third amino acids. This is repeated, and after a peptide having a target length is synthesized, all of the functional groups are deprotected.

Examples of the resin for solid-phase synthesis include Merrifield resin, MBHA resin, Cl-Trt resin, SASRIN resin, Wang resin, Rink amide resin, HMFS resin, Amino-PEGA resin (Merck KGaA), HMPA-PEGA resin (Merck KGaA), and the like. These resins may be used after being washed using a solvent (dimethylformamide (DMF), 2-propanol, methylene chloride, and the like).

Examples of the protecting group of the α-amino group include the benzyloxycarbonyl (Cbz or Z) group, tert-butoxycarbonyl (Boc) group, fluorenylmethoxycarbonyl (Fmoc) group, benzyl group, allyl group, allyloxycarbonyl (Alloc) group, and the like. The Cbz group may be deprotected by a treatment using hydrofluoric acid, hydrogenation, or the like, the Boc group may be deprotected by a treatment using trifluoroacetic acid (TFA), and the Fmoc group may be deprotected by a treatment using pipericine or pyrrolysine.

Examples such as methyl ester, ethyl ester, allyl ester, benzyl ester, tert-butyl ester, cyclohexyl ester, and the like may be used to protect the α-carboxy group.

Activation of the carboxy group may be performed using a condensing agent. Examples of the condensing agent include dicyclohexylcarbodiimide (DCC), diisopropylcarbodiimide (DIC), 1-ethyl-3-(3-dimethylaminopropyl)carbodiimide (EDC or WSC), (1H-benzotriazole-1-yloxy)tris(dimethylamino)phosphonium hexafluorophosphate (BOP), 1-[bis(dimethylamino)methyl]-1H-benzotriazolium-3-oxide hexafluorophosphate (HBTU), and the like.

Cleavage of the peptide chain from the resin may be performed by treating the peptide chain using an acid such as TFA, hydrogen fluoride (HF), or the like.

Production of a peptide by a gene recombination method (translation/synthesis system) may be performed using a nucleic acid encoding the peptide. The nucleic acid encoding the peptide may be DNA or RNA.

The nucleic acid encoding the peptide may be prepared by a known method or a method equivalent thereto. For example, the peptide may be synthesized by an automated synthesizer. A restriction enzyme recognition site may be added to insert the obtained DNA into a vector. Alternatively, a base sequence encoding an amino acid sequence for splicing a formed peptide chain using an enzyme or the like may be incorporated.

As described above, when the peptide is fused to a cell-penetrating peptide or the like, the nucleic acid also includes a nucleic acid encoding the cell-penetrating peptide.

A chimeric protein expression method for expressing the target peptide as a chimeric peptide of another peptide may also be used to suppress degradation by a host-derived protease. In this case, a nucleic acid encoding the target peptide and the peptide bound thereto may be used as the nucleic acid.

Subsequently, an expression vector is prepared using the nucleic acid encoding the peptide. The nucleic acid may be digested as is or by a restriction enzyme, and alternatively, the nucleic acid may be inserted downstream of a promotor of the expression vector by adding a linker, or the like. Examples of the vector include an *Escherichia coli*-derived plasmid (pBR322, pBR325, pUC12, pUC13, pUC18, pUC19, pUC118, pBluescript II, and the like), a *Bacillus subtilis*-derived plasmid (pUB110, pTP5, pC1912, pTP4, pE194, pC194, and the like), a yeast-derived plasmid (pSH19, pSH15, YEp, YRp, YIp, YAC, and the like), a bacteriophage (e phage, M13 phage, and the like), a virus (retrovirus, vaccinia virus, adenovirus, adeno-associated virus (AAV), cauliflower mosaic virus, tobacco mosaic virus, baculovirus, and the like), a cosmid, and the like.

The promoter may be selected appropriately according to the type of host. When the host is an animal cell, for example, a promoter derived from SV40 (simian virus 40) or a promoter derived from CMV (cytomegalovirus) may be used. When the host is *Escherichia coli*, a trp promoter, a T7 promoter, a lac promoter, or the like may be used.

The expression vector may incorporate, for example, a DNA replication starting point (ori), a selective marker (antibiotic resistance, auxotrophy, or the like), an enhancer, a splicing signal, a poly-A addition signal, a nucleic acid encoding a tag (FLAG, HA, GST, GFP, or the like), or the like.

Next, an appropriate host cell is transformed by the expression vector. The host may be appropriately selected in relation to the vector. Examples such as *Escherichia coli*, *Bacillus subtilis* (*Bacillus*), yeast, insects or insect cells, animal cells, or the like may be used as the host. As the animal cells, for example, HEK293T cells, CHO cells, COS cells, myeloma cells, HeLa cells, and Vero cells may be used. Transformation may be carried out according to a known method, such as a lipofection method, a calcium phosphate method, an electroporation method, a microinjection method, a gene gun method, or the like depending on the type of host. The target peptide is expressed by culturing a transformant according to a conventional method.

As for purification of the peptide from the transformant culture, cultured cells are recovered and then suspended in an appropriate buffer solution, followed by disruption of cells by a method such as sonication, freeze-thawing, or the like, and then a crude extract is obtained by centrifugation or filtration. When the peptide is secreted into the culture solution, a supernatant is recovered.

Purification of the crude extract or the culture supernatant may also be performed by a known method or a method equivalent thereto (for example, salting-out, dialysis, an ultrafiltration method, gel filtration method, SDS-PAGE method, ion exchange chromatography, affinity chromatography, reversed-phase high-performance liquid chromatography, and the like).

The obtained peptide may be converted from a free body to a salt or from a salt to a free body by a known method or a method equivalent thereto.

In one aspect, the translation/synthesis system may be a cell-free translation system. According to the cell-free translation system, a highly pure form of an expression product can generally be obtained without purification. The cell-free translation system includes, for example, a ribosome protein, an aminoacyl-tRNA synthase (ARS), a ribosome RNA, an amino acid, rRNA, GTP, ATP, a translation initiation factor (IF), an elongation factor (EF), a release factor (RF), and a ribosome regeneration factor (RRF), or another factor required for translation. An *Escherichia coli* extract or a wheat embryo extract may be added to increase expression efficiency. In addition, a rabbit red blood cell extract or an insect cell extract may be added.

By continuously supplying energy to a system including these using dialysis, a protein of several hundred μg to several mg/mL may be produced in a non-limiting manner. The system may include an RNA polymerase to concurrently perform transcription of genomic DNA. Examples of commercially available cell-free translation systems that may be used include RTS-100 (registered trademark) by Roche Diagnostics K.K., PURE System by GeneFrontier Corporation, PURExpress In Vitro Protein Synthesis Kit by New England Biolabs Inc., and the like for a system derived from *Escherichia coli*, and a system by ZOIGENE, CellFree Sciences Co., Ltd., or the like for a system using wheat embryo extract.

In the cell translation system, artificial aminoacyl-tRNA may be used and a desired amino acid or hydroxy acid may be linked (acylated) to a tRNA in place of an aminoacyl-tRNA synthesized by a natural aminoacyl-tRNA synthase. The aminoacyl-tRNA may be synthesized using an artificial ribozyme.

An example of the ribozyme includes a flexizyme (flexizyme) (H. Murakami, H. Saito, and H. Suga, (2003), Chemistry & Biology, Vol. 10, 655-662; and WO 2007/066627 and the like), all incorporated herein by reference. Flexizymes are also known under the names of prototype flexizyme (Fx), newly modified dinitrobenzyl flexizyme (dFx), enhanced flexizyme (eFx), aminoflexizyme (aFx), and the like.

A desired codon may be translated in association with the desired amino acid or hydroxy acid by using the tRNA produced by flexizyme and to which the desired amino acid or hydroxy acid is linked. A specialty amino acid may be used as the desired amino acid. For example, an unnatural amino acid required for the above circularization may also be introduced into the binding peptide by this method.

Various methods commonly used in the technical field may be used for chemical synthesis of the peptide, including, for example, stepwise solid-phase synthesis, semisynthesis of peptide fragments undergoing conformationally supported religation, and chemical ligation. Synthesis of the peptide is chemical synthesis using various solid phase technologies described in, for example, K. J. Jensen, P. T. Shelton, S. L. Pedersen, Peptide Synthesis and Applications, 2nd Edition, Springer, 2013, and the like. A preferable strategy is based on a combination of an Fmoc group capable of temporarily protecting the α-amino group and being selectively removed using a base, and a protecting group that temporarily protects a side chain functional group and is stable under Fmoc deprotection conditions. Selection of this kind of general peptide side chain is known according to the aforementioned Peptide Synthesis and Applications, 2nd Edition; G. B. Fields, R. L. Noble, Solid Phase Peptide Synthesis Utilizing 9-Fluorenylmethoxycarbonyl Amino Acids, Int. J. Peptide Protein Res. 35, 1990, 161-214, and the like; however, preferable peptide side chain protecting groups include, for example, a benzyl group or a tert-butyl group and a trityl (Trt) group for the hydroxy group of serine or threonine; a 2-bromobenzyloxycarbonyl group or a tert-butyl group for the hydroxy group of tyrosine; a Boc group, a methyltetrazole thiol (Mtt) group, an Alloc group, and an ivDde group for the amino group of the lysine side chain; a Trt group or a Boc group for the imidazole group of histidine; a 2,2,4,6,7-pentamethyldihydrobenzofuran-5-sulfonyl group (Pbf) group for the guanidyl group of arginine; a tert-butyl group, an allyl group, and a 3-methylpentane (Mpe) group for carboxyl groups, such as glutamic acid and aspartic acid; a Trt group for the carboxamide group of glutamine or asparagine; or a Trt group and a monomethoxytrityl (Mmt) group for the thiol group of cysteine.

The peptide may be synthesized by a stepwise method on the solid-phase resin described above. The C-terminal amino acid to be used and all of the amino acids or peptides to be used for synthesis must be selectively removed during the process of synthesizing the α-amino protecting group. Preferably, the solid-phase resin described above is used, and once a C-terminal carboxyl group of a peptide having its N-terminal properly protected by Fmoc or the like or a C-terminal carboxyl group of an amino acid having its N-terminal protected by Fmoc is made into an activated ester by an appropriate reagent, this is then added to the amino group on the solid-phase resin to start. Subsequent elongation of the peptide chain may be achieved by removing the N-terminal protecting group (Fmoc group) then successively repeating condensation of the protected amino acid derivative according to the amino acid sequence of the target peptide. Note that these may release the target peptide in a final stage. Examples of releasing conditions are given in Teixeira, W. E. Benckhuijsen, P. E. de Koning, A. R. P. M. Valentijn, J. W. Drijfhout, Protein Pept. Lett., 2002, 9, 379-385, and the like, and the peptide may be released in a TFA solution containing water/silyl hydride/thiol as a scavenger in TFA. Typical examples include TFA/Water/TIS/DODT (volume ratio 92.5:2.5:2.5:2.5).

Synthesis of the peptide described in the present specification may be carried out using a single or multi-channel peptide synthesizer, for example, a Liberty Blue synthesizer from CEM Corporation, a Syro I synthesizer or a successor machine thereof from Biotage Japan, Ltd., or the like.

Activation of the carboxy group may be performed using a condensing agent. Examples of the condensing agent include dicyclohexylcarbodiimide (DCC), diisopropylcarbodiimide (DIPCDI), 1-ethyl-3-(3-dimethylaminopropyl) carbodiimide (EDC or WSC), (1H-benzotriazole-1-yloxy) tris(dimethylamino)phosphonium hexafluorophosphate (BOP), 1-[bis(dimethylamino)methyl]-1H-benzotriazolium-3-oxide hexafluorophosphate (HBTU), and the like.

Cyclization of the peptide may be carried out according to a known method. In a non-limiting manner, by designing the peptide to comprise two or more cysteine residues, for example, a cyclic structure may be formed by a disulfide bond after translation. Furthermore, according to the method of Goto et al. (Y. Goto, et al. ACS Chem. Biol. 3 120-129 (2008)), a peptide having a chloroacetyl group at its N-terminal may be synthesized by genetic code reprogramming technology and may also be circularized by disposing a cysteine residue containing a sulfur molecule in the peptide. Thus, a mercapto group spontaneously performs a nucleophilic attack on the chloroacetyl group after translation, and the peptide is circularized by thioether binding. Other amino acid combinations that bind to form a ring may be disposed within the peptide and circularized by genetic code reprogramming technology. Alternatively, circularization may be carried out by disposing an L-2-aminoadipic acid residue in the peptide and binding it to the main chain amino group of the N-terminal. In this manner, a known circularization method may be used without any particular limitation.

Pharmaceutical Composition

The present technology also relates to a pharmaceutical composition that comprises the peptide of the present technology. Diseases targeted by the pharmaceutical composition of the present technology are those associated with human growth hormone hypersecretion, and which exhibits various symptoms due to excessive secretion of growth hormone, and preferably pituitary somatotropin hypersecretion, which is caused by tumors and inflammation of the pituitary gland and the like. Furthermore, the target includes diseases that are caused by excessive secretion of growth hormone, for example, acromegaly (acromegaly) or gigantism. The peptide of the present technology is useful as an active ingredient of a pharmaceutical composition for treating diseases that are associated with human growth hormone hypersecretion, and acromegaly and gigantism.

In some embodiments, the pharmaceutical composition has GhR antagonistic activity. In some embodiments, the pharmaceutical composition has hGhR antagonistic activity.

Growth hormone is secreted into the bloodstream when produced in the pituitary gland and binds to the growth hormone receptor (GhR) that is expressed on various cell surfaces, such as the liver, muscle tissue, and bone tissue. Binding of GH and GhR induces the production of insulin-like growth factor-1 (IGF-1) in cells, particularly in liver cells. In acromegaly and gigantism described below, elevated growth hormone levels in plasma and/or tissue are known to be is associated with elevated IGF-I levels in plasma and/or tissue.

Excessive or insufficient secretion of GH is known to cause disease. Excessive secretion of GH causes a condition called acromegaly (which may be called gigantism when developed in children), which presents with symptoms such as excessive bone elongation, soft tissue hypertrophy, cardiovascular and gastrointestinal pathologies, and insulin resistance. In many cases, this condition is due to growth hormone-secreting cells becoming tumorigenic (pituitary tumor) while retaining their secretory function, and the frequency of onset is as rare as 4 to 24 per 100,000 people. When not properly treated, there is a high possibility of complications of metabolic diseases such as diabetes and hypertension, angina, myocardial infarction, conditions falling under cerebrovascular disorder, cancer of colon and thyroid, and the like, so early diagnosis and treatment are required.

The most common treatment for acromegaly is surgical resection of pituitary tumors. However, tumors may be large and thus difficult to resect, or GH secretion may remain excessive even after resection, and in these cases, drug therapy is employed.

A compound having an activity of inhibiting GhR and a composition comprising such for the treatment of acromegaly and gigantism have been desired. Therefore, the present specification also discloses the foregoing peptide that has GhR antagonistic activity and a pharmaceutical composition for the treatment of diseases associated with human growth hormone hypersecretion, preferably acromegaly and gigantism. In some embodiments, the pharmaceutical composition of the present technology is a pharmaceutical composition for the treatment of a disease associated with human growth hormone hypersecretion. In some embodiments, the pharmaceutical composition of the present technology is for the treatment of acromegaly or gigantism.

As used herein, the expression "a disease associated with human growth hormone hypersecretion" refers to a disease that exhibits various symptoms mainly caused by excessive peripheral hormone due to hypersecretion of one or multiple hormones from the pituitary gland. Pathoetiology includes disorders of the pituitary gland itself, disorders of the hypothalamus that controls the secretion of pituitary hormones, and disorders of the pituitary stalk that connects the pituitary gland and hypothalamus, and also combinations thereof. Since the peptide of the present technology induces a therapeutic effect by binding to the growth hormone receptor, the pathoetiology is not particularly limited.

"Acromegaly" is a condition that is caused by hypersecretion of growth hormone and may be called gigantism when developed during childhood. In children, when acromegaly develops prior to puberty, long bone elongation does not stop and the height and limbs grow to an abnormal length; however, in acromegaly, which develops in adults, the bones become deformed or enlarged rather than elongate. Also, enlargement of non-bone tissue can occur, for example, acromegaly may cause cardiac failure due to the heart dilating, or visual impairment, weakness of limbs, and the like due to the enlarged tissue compressing the nerves. In addition, it is known that diabetes, hypertension, sleep apnea syndrome, tumors that may become cancerous, and the like are more likely to develop. Therefore, performing a treatment using a pharmaceutical composition that contains the peptide of the present technology for a disease associated with human growth hormone hypersecretion (such as for example, but not limited to, a disease associated with an increase in expression, production and/or secretion of human growth hormone) may, as a result, lead to the prevention of cardiac failure, diabetes, hypertension, sleep apnea syndrome, and specific (in particular, colon) tumors caused by acromegaly and gigantism.

In some embodiments, the pharmaceutical composition of the present technology may comprise the peptide itself or may comprise a pharmaceutically acceptable salt of the peptide. The "peptide" in the present specification may comprise a pharmaceutically acceptable salt of the peptide unless otherwise specified. The pharmaceutical composition preferably comprises the peptide as an active ingredient in an effective amount.

The salt of the peptide (pharmaceutically acceptable salt) is preferably an acid addition salt. For example, a salt of an inorganic acid (such as hydrochloric acid, phosphoric acid, hydrobromic acid, sulfuric acid), a salt of an organic acid (such as acetic acid, formic acid, propionic acid, fumaric acid, maleic acid, succinic acid, tartaric acid, citric acid, malic acid, oxalic acid, benzoic acid, methanesulfonic acid, benzenesulfonic acid), or the like is used as this salt. The peptide or a salt thereof also comprises a solvate such as a hydrate.

In the present specification, the form of administration of the pharmaceutical composition is not particularly limited and may be oral or parenteral. Examples of parenteral administration include injection, such as intramuscular injection, intravenous injection, or subcutaneous injection; transdermal administration; transmucosal administration (transnasal, transoral, transocular, transpulmonary, transvaginal, or transrectal); or the like.

The pharmaceutical composition may be modified in various ways, considering a property where a polypeptide is easily metabolized and excreted. For example, polyethylene glycol (PEG) or a sugar chain may be added to the polypeptide to extend its retention time in the blood to reduce antigenicity. Furthermore, an emulsion, nanoparticles, nanospheres, or the like prepared in a biodegradable polymerized compound such as polylactic acid/glycol (PLGA), porous hydroxyapatite, liposomes, surface-modified liposomes, and unsaturated fatty acids are used as a controlled-release base, and the polypeptide may be present in the base. In the case of transdermal administration, a weak current is allowed to pass through the skin surface and penetrate the stratum corneum (iontophoresis).

As for the pharmaceutical composition, the active ingredient may be used as is, or the pharmaceutical composition may comprise a pharmaceutically acceptable carrier, an excipient, an additive, or the like, or may be formulated. Examples of the dosage form include a liquid agent (for example, an injection), a dispersant, a suspension, a tablet, a pill, a powder, a suppository, a powdered drug, a fine granule, a granule, a capsule, a syrup, a lozenge, an inhalant, an ointment, an eye drop, a nasal drop, an ear drop, a patch, or the like. The formulation may be carried out by a common method using, for example, an excipient, a binder, a disintegrant, a lubricant, a dissolving agent, a solubilizing agent, a colorant, a flavoring agent, a stabilizer, an emulsifier, an absorption promoter, a surfactant, a pH regulator, a preservative, an antioxidant, or the like as appropriate.

Examples of ingredients used for formulation include but are not limited to purified water, saline, phosphate buffer solution, dextrose, glycerol, a pharmaceutically acceptable organic solvent such as ethanol, animal and vegetable oil, lactose, mannitol, glucose, sorbitol, crystalline cellulose, hydroxypropyl cellulose, starch, corn starch, anhydrous silicic acid, magnesium aluminum silicate, collagen, polyvinyl alcohol, polyvinyl pyrrolidone, carboxyvinyl polymer, sodium carboxymethylcellulose, sodium polyacrylate, sodium alginate, water-soluble dextran, sodium carboxymethyl starch, pectin, methyl cellulose, ethyl cellulose, xanthan gum, gum arabic, tragacanth, casein, agar, polyethylene glycol, diglycerin, glycerin, propylene glycol, vaseline, paraffin, octyldodecyl myristate, isopropyl myristate, higher alcohol, stearyl alcohol, stearic acid, human serum albumin, or the like.

The pharmaceutical composition may comprise an absorption promoter for improving absorption of a poorly absorbable drug, in consideration of the fact that it is generally difficult for peptides to be absorbed through mucous membranes. The following may be used as the absorption promoter: a surfactant such as polyoxyethylene lauryl ether, sodium lauryl sulfate, and saponin; a bile salt such as glycocholic acid, deoxycholic acid, and taurocholic acid; a chelating agent such as EDTA and salicylic acid; a fatty acid such as caproic acid, capric acid, lauric acid, oleic acid, linoleic acid, a mixed micelle; an enamine derivative, an N-acyl collagen peptide, an N-acyl amino acid, a cyclodextrin, chitosan, a nitric oxide donor, or the like.

When the pharmaceutical composition is a pill or tablet, it may be coated using a sugar coating, or a gastric-soluble or enteric-coated substance.

When the pharmaceutical composition is an injection, it may comprise distilled water for injection, physiological saline, propylene glycol, polyethylene glycol, vegetable oil, alcohol, or the like. Additionally, a humectant, an emulsifier, a dispersant, a stabilizer, a dissolving agent, a solubilizing agent, a preservative, or the like may be added.

Furthermore, the pharmaceutical composition may be targeted not only to humans but also to non-human mammals or birds. Examples of non-human mammals include primates other than humans (monkeys, chimpanzees, gorillas, and the like), livestock animals (pigs, cows, horses, sheep, and the like), dogs, cats, rats, mice, guinea pigs, rabbits, and the like.

In particular, the dosage in the case of administering to a human changes depending on symptoms, age, sex, and weight of the patient, sensitivity difference, administration method, administration interval, type of active ingredient, and type of formulation, and it may be administered in a non-limiting manner: for example, by administering between about 30 µg to about 100 g, between about 1 µg to about 10 g, between about 1 µg to about 1 g, between about 10 µg to about 1 g, between about 10 µg to about 500 mg, between about 100 µg to about 10 g, between about 100 µg to about 1 g, between about 10 µg to about to about 500 mg, between about 100 µg to about 500 mg, or between about 100 µg to about 100 mg once or divided into several doses. In the case of injection, between about 1 µg/kg and about 3,000 µg/kg or between about 3 µg/kg and about 1,000 µg/kg according to the bodyweight of the patient may be administered once or divided into several doses.

The present technology also relates to a method for treating a disease associated with human growth hormone hypersecretion by administering the peptide of the present technology to a subject.

The present technology also relates to a use of the peptide of the present technology for the treatment of a disease associated with human growth hormone hypersecretion.

The present technology also relates to a use of the peptide for manufacturing a pharmaceutical composition for the treatment of a disease associated with human growth hormone hypersecretion.

The present technology also relates to the peptide of the present technology for use in a method for treating a disease associated with human growth hormone hypersecretion.

EXAMPLES

The present technology is described in detail below based on examples, but the present technology is not limited to these examples. A person having ordinary skill in the art is capable of easily adding modifications and changes to the present technology based on the description of the present specification, and these are included in the technical scope of the present technology.

Example 1—Chemical Synthesis

Synthesis may be completed using commercially available products as is for all raw materials, building blocks, reagents, acids, bases, solid-phase resins, and solvents used in chemical synthesis in the following examples, or by a person having ordinary skill in the art using organic chemistry techniques. Note that commercial products were used for amino acids containing protecting groups unless otherwise specified.

Elongation of the peptide chain in a solid-phase resin is performed by using the resin described in each example as a starting material and using a standard peptide coupling reaction condition and Fmoc removal reaction condition. Reactions were carried out using Liberty Blue, an automated peptide synthesizer manufactured by CEM, in accordance with the manufacturer's manual. As an example, some of the common amino acids used are listed below, and side chain protecting groups are shown in parentheses:
  Fmoc-N-Me-Lys(alloc)-OH;
  Fmoc-Tyr(tBu)-OH;
  Fmoc-F4COO(tBu)-OH;
  Fmoc-Val-OH;
  Fmoc-Ser(tBu)-OH;
  Fmoc-Asn(Trt)-OH;
  Fmoc-W1aa(allyl)-OH;
  Boc-Lys(Fmoc)-OH;
  Fmoc-Lys(ivDde)-OH;
  Fmoc-Lys(Boc)-OH;
  Fmoc-Lys(alloc)-OH;
  Fmoc-W5H-OH;
  Fmoc-Glu-OtBu;
  Fmoc-Aib-OH;
  Fmoc-A4pipaa(tBu)-OH;
  Fmoc-W7N-OH;
  Fmoc-W5OMe-OH;
  Fmoc-Cys(Trt)-OH;
  Fmoc-Gly-OH;
  Fmoc-Pro-OH; and
  Fmoc-ds(tBu)-OH.

Reversed-phase separation HPLC was carried out as the method for purifying the obtained crude purified peptide using an AutoPurification System-SQD2 single quadruple mass spectrometer, manufactured by Waters, and elution was performed while monitoring m/z ions derived from the target product. It was confirmed that the mass spectrum obtained in ESI-positive scanning mode and the mass spectrum containing polyvalent ions calculated by the molecular formula of the target product matched within the error range of the mass spectrometer used. Note that the purification conditions including the columns used are shown in the respective examples.

As for the structure determination of chemically synthesized peptides, the molecular weight calculated in consideration of the amino acid used according to the target sequence and the building block used as necessary was confirmed by ESI-MS(+) in the mass spectrum analysis method. Note that "ESI-MS(+)" indicates an electrospray ionization mass spectrometry method performed in positive ion mode. The detected mass is reported in "m/z" units. Note that compounds having a molecular weight greater than approximately 1,000 are frequently detected as bivalent ions or trivalent ions.

Example 2—Identification of hGhR Binding Peptides

Growth hormone receptor (GhR) binding peptides were screened and identified by a screening method similar to that described in Patent Document WO2014/119600, WO2012/033154, and WO2007/066627, all of which are incorporated herein by reference. In this screen, recombinant human GhR protein (R&D systems) fused to Fc portion of human IgG was used as a bait protein to enrich GhR binding peptides. The binding of the peptides obtained from the screening was first tested with in-vitro translated peptide fused to DNA/RNA tag expressed from singleton DNA template. The in-vitro translated peptide was incubated with human GhR-Fc immobilized on ProteinG magnetic beads, and the amount of the peptide coprecipitated with the beads was quantified by qPCR. Then, the peptides were chemically synthesized in order to confirm quantitively whether they have binding activity to GhR.

Example 3—Synthesis of GhR Binding Peptides

For all raw materials, building blocks, reagents, acids, bases, solid phase resins, and solvents used in the chemical synthesis in the following examples, commercially available products were used as they were, or organic chemical methods were used by those skilled in the art. Unless otherwise specified, commercially available amino acids containing protecting groups were used as they were.

For the structure determination of the chemically synthesized peptide, the molecular weight calculated in consideration of the amino acids used according to the target sequence and the building blocks used as needed was confirmed by ESI-MS (+) in the mass spectrum analysis method. Note that "ESI-MS (+)" indicates an electrospray ionization mass spectrum analysis method performed in the positive ion mode. The detected mass was reported in "m/z" units. Compounds having a molecular weight greater than about 1000 were frequently detected as divalent ions or trivalent ions. Column: CORTECS® UPLC® C18 column (Japan Waters), 90 Å, 1.6 µm, 2.1×100 mm; Mobile Phase: MeCN/0.025% TFA in H2O; Temperature: 40° C.; Gradient: 5-95% MeCN/0.025% TFA in $H_2O$ in 5.56 min; linear gradient, Flow rate: 0.4 mL/min, Detection: UV 220 nm. Peptide synthesis was performed in accordance with a common solid-phase synthesis method using: Sieber Amide resin (product of Novabiochem): 9-fluorenylmethoxycarbonyl group (Fmoc) as a protecting group of an α amino group; and an automated Liberty Blue (CEM Inc.).

The GhR binding peptides were synthesized: Peptide synthesis was performed in accordance with a common solid-phase synthesis method using: Sieber Amide resin (product of Novabiochem): 9-fluorenylmethoxycarbonyl group (Fmoc) as a protecting group of an α amino group; 20% piperidine in DMF for Fmoc deprotection; 4.2 equivalents of Fmoc-amino acid, 4 equivalents of Oxyma Pure, and 8 equivalents of N,N"-Diisopropylcarbodiimide (DIC) as coupling reagents for peptide elongation; and an automated Liberty Blue (CEM Inc.).

The cyclic peptide was purified by reverse-phase high-performance liquid chromatography (HPLC) using AutoPurification System—SQD2 single quadruple mass spectrometer (product of Waters) to obtain an intended product. The peptide thus obtained was identified by the mass spectrum obtained in the ESI-positive scan mode and the mass spectrum containing polyvalent ions calculated from the molecular formula of the target object were in agreement within the error range of the mass spectrometer used. Column: Kinetex EVO C18 2.6 um, 2.1 ID×150 mm, 100 Å (with a guard cartridge 2.1 mmID), Mobile Phase A: 0.025% TFA in H2O, Mobile Phase B: 0.025% TFA in MeCN. Temperature: 60° C., Gradient: 20-60% B over 7.15 min, 60-95% B over 0.3 min, 95% B over 1.55 min, 95-20% B over 0.01 min, then 20% B over 3.49 min, Flow rate: 0.5 mL/min, Detection: UV 225 nm, 20-60/7.15 min, 60-95/0.3 min, 95-95/1.55 min, 95-20/0.01 min, 20-20/3.49 min.

Synthesis of bicyclic peptides (Compound No. 1-32 in Table 1-1) are performed as described below.

Synthesis of PD-217 (Table 1-1 Compound No. 9); Compound Including Bicyclic Peptide (Peptide SEQ ID No. 10) and Albumine Binder (E_E_4IPhpCO) Conjugated Linker (Lysine)

To the reaction vessel containing the resin was added 20% piperidine in DMF and the mixture was stirred. The synthesis was started from Boc-Lys (Fmoc)-OH using a common solid-phase synthesis. Double coupling was conducted at position 1, 3, 10, and 11 from N-terminal amino acid.

After N-terminal Fmoc-F4COO(tBu)-OH was linked, 0.25 equivalents of (Pd(PPh$_3$)$_4$), 15 equivalents of PhSiH$_3$, and DCM were added and the resulting mixture was allowed to agitate to remove alloc and allyl group on the side chain of N-methyl-L-lysine and 1-(carboxymethyl)-L-tryptophan, respectively. The peptide resin thus obtained was treated with 16 equivalents of DIC and 8 equivalents of Oxyma pure in DMF under microwave irradiation.

After the Fmoc group was deprotected with 20% piperidine in DMF, the resin was washed with DMF. Then to the resin was added 5 equivalents of 2-chloroacetic acid, 5 equivalents of DIC, and 5 equivalents of HOSu in DCM/NMP (1:1 v/v). The resin was successively washed with DMF and DCM and then dried.

[CHEM 1]

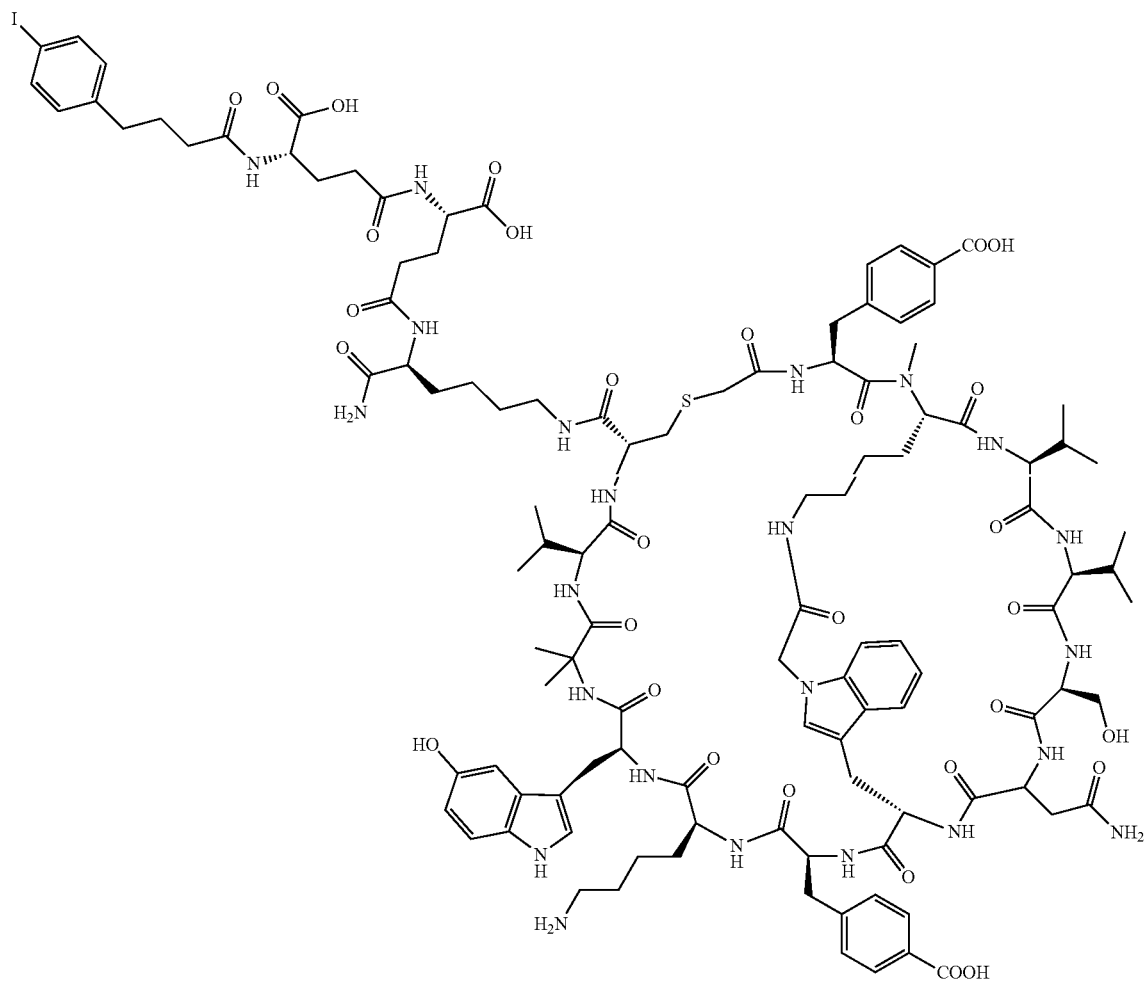

Fmoc amino acids used in the synthesis included Boc-Lys(Fmoc)-OH; Fmoc-Cys(Trt)-OH; Fmoc-Val-OH; Fmoc-Aib-OH; Fmoc-W5H-OH; Fmoc-Lys(ivDde)-OH; Fmoc-F4COO(tBu)-OH; Fmoc-W1aa(allyl)-OH; Fmoc-Asn(Trt)-OH; Fmoc-Ser(tBu)-OH; Fmoc-MeK(alloc)-OH.

TFA-water-TIS-DODT mixture (92.5:2.5:2.5:2.5 v/v/v/v) was added and the resulting mixture was stirred at room temperature for 1.25 hours.

The crude peptide was cleaved from resin was collected by ether precipitation. After washing three times with diisopropyl ether and drying, a DMSO-water-MeCN (1:1:1 v/v/ v) containing 15 equivalents of triethylamine was added to give a final concentration of 5 mM, followed by stirring at room temperature for 2 hours.

After the solvent was removed, a solution of DMSO-water (9:1 v/v), 1.02 equivalents of 1-(tert-butyl) 5-(2,5-dioxopyrrolidin-1-yl) ((S)-5-(tert-butoxy)-4-(4-(4-iodophenyl)butanamido)-5-oxopentanoyl)-L-glutamate, and 3 equivalents of N-ethyl-N-isopropylpropan-2-amine were added and the mixture was stirred for 1 hour. The solution was concentrated, the product was reprecipitated from ether and dried.

A TFA-water-TIS-DODT mixture (92.5:2.5:2.5:2.5 v/v/v/v) was added and the resulting mixture was stirred at room temperature for 30 minutes. The peptide was collected by ether precipitation and dried under reduced pressure.

The ivDde group on Lysine at position 9 from N-terminal amino acid was cleaved with 25 equivalents of hydrazine monohydrate in DMSO. After the mixture was stirred for 2.5 hours, the reaction was quenched with 40 equivalents of acetic acid. The crude peptide was confirmed by analysis conditions by LCMS: retention time=1.48 min.

The crude peptide was purified by the reverse-phase HPLC and the product was confirmed as shown in the following by HPLC under the conditions. Analysis HPLC condition: retention time=4.220 min. MS (ESI+); calcd. for $[M+2H]^{2+}$ 1242.8, found 1242.6.

Synthesis of PD-233 (Table 1-1 Compound No. 11); Compound Including Bicyclic Peptide (Peptide SEQ ID No. 10) and Albumine Binder (E-E-cC14COO) Conjugated Linker (Lysine)

Fmoc amino acids used in the synthesis included Fmoc-Lys(alloc)-OH; Fmoc-Glu-OtBu; Fmoc-Cys(Trt)-OH; Fmoc-Val-OH; Fmoc-Aib-OH; Fmoc-W5H-OH; Fmoc-Lys(Boc)-OH; Fmoc-F4COO(tBu)-OH; Fmoc-W1aa(allyl)-OH; Fmoc-Asn(Trt)-OH; Fmoc-Ser(tBu)-OH; Fmoc-MeK(alloc)-OH.

To the reaction vessel containing the resin was added 20% piperidine in DMF and the mixture was stirred. The synthesis was started from Fmoc-Lys(alloc)-OH using a common solid-phase synthesis method. Double coupling was conducted at position 1, 3, and 11 from N-terminal amino acid.

After two Fmoc-Glu-OtBu monomers (CAS: 84793-07-7) and 16-(tert-butoxy)-16-oxohexadecanoic acid (CAS: 843666-27-3) were linked to Fmoc-Lys(alloc)-OH, 0.25 equivalents of $Pd(PPh_3)_4$, 15 equivalents of $PhSiH_3$, and DCM were added and the resulting mixture was allowed to agitate to remove alloc group on the side chain of lysine. The peptide resin thus obtained was used in the further peptide synthesis.

After N-terminal Fmoc-F4COO(tBu)-OH was linked, 0.25 equivalents of $Pd(PPh_3)_4$, 15 equivalents of $PhSiH_3$, and DCM were added and the resulting mixture was allowed to agitate to remove alloc and allyl group on the side chain of MeK and W1aa, respectively. The peptide resin thus obtained was treated with 16 equivalents of DIC, and 8 equivalents of Oxyma pure DMF under microwave irradiation.

After the Fmoc group was deprotected with 20% piperidine in DMF, the resin was washed with DMF. Then to the resin was added 5 equivalents of 2-chloroacetic acid, 5

[CHEM 2]

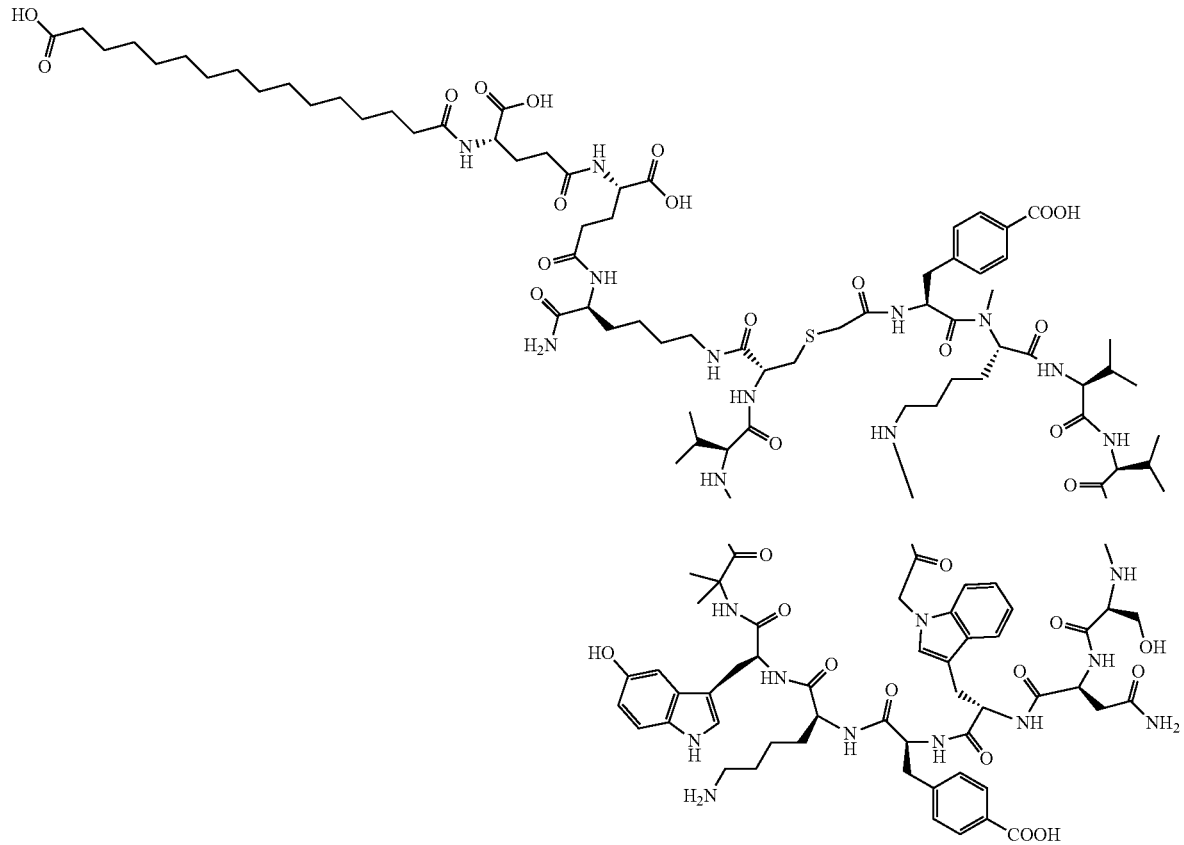

equivalents of DIC, and 5 equivalents of HOSu in DCM/NMP (1:1 v/v). The resin was successively washed with DMF and DCM and then dried.

A TFA-water-TIS-DODT mixture (90:2.5:2.5:5 v/v/v/v) was added and the resulting mixture was stirred at room temperature for 1.25 hours.

The crude peptide was cleaved from resin was collected by ether precipitation. After washing three times with diisopropyl ether and drying, a DMSO-water-MeCN (2:1:1 v/v/v) containing 15 equivalents of triethylamine was added to give a final concentration of 5 mM, followed by stirring at room temperature for 4 hours. The crude peptide was confirmed by analysis conditions by LCMS: retention time=2.36 min.

The crude peptide was purified by the reverse-phase HPLC and the product was confirmed as shown in the following by HPLC under the following conditions. Analysis HPLC condition: retention time=4.892 min.

MS (ESI+); calcd. for [M+2H]$^{2+}$ 1240.1, found 1240.8.

Synthesis of monocyclic peptides (Compound No. 34-58 in Table 1-2) are performed as described below;
Synthesis of PD-209 (Table 1-2 Compound No. 54); Compound Including Albumine Binder (E-4IPhpCO) Conjugated Monocyclic peptide (Peptide SEQ ID No.31) and Linker (SEQ ID No. 32)

Fmoc amino acids used in the synthesis included Fmoc-ds(tBu)-OH; Fmoc-Pro-OH; Fmoc-Gly-OH; Fmoc-Cys(Trt)-OH; Fmoc-Val-OH; Fmoc-Aib-OH; Fmoc-W5H-OH; Fmoc-Lys(Boc)-OH; Fmoc-F4COO(tBu)-OH; Fmoc-W5OMe-OH; Fmoc-Asn(Trt)-OH; Fmoc-Ser(tBu)-OH; Fmoc-MeK(alloc)-OH; Fmoc-Tyr(tBu)-OH.

To the reaction vessel containing the resin was added 20% piperidine in DMF and the mixture was allowed to be agitated. The synthesis was started from Fmoc-ds(tBu)-OH using a common solid-phase synthesis method. Double coupling was conducted at position 1, 3, 5, 10, 11, 14, and 16 from N-terminal amino acid.

After N-terminal Fmoc-Tyr(tBu)-OH was linked, 20% piperidine in DMF was added. The resin was washed with DMF, then 5 equivalents of 2-chloroacetic acid, 5 equivalents of DIC, and 5 equivalents of N-hydroxysuccinimide (HOSu) in methylene chloride (DCM)/1-Methyl-2-pyrrolidone (NMP) (1:1 v/v) were added. The resin was successively washed with DMF and DCM.

To a reaction vessel containing the resin was added 0.25 equivalents of tetrakis(triphenylphosphine)palladium(0) (Pd (PPh$_3$)$_4$), 15 equivalents of phenylsilane, and DCM and the resulting mixture was allowed to agitate to remove allyloxycarbonyl (alloc) group on the side chain of MeK. The peptide resin thus obtained was treated with 4 equivalents of

[CHEM 3]

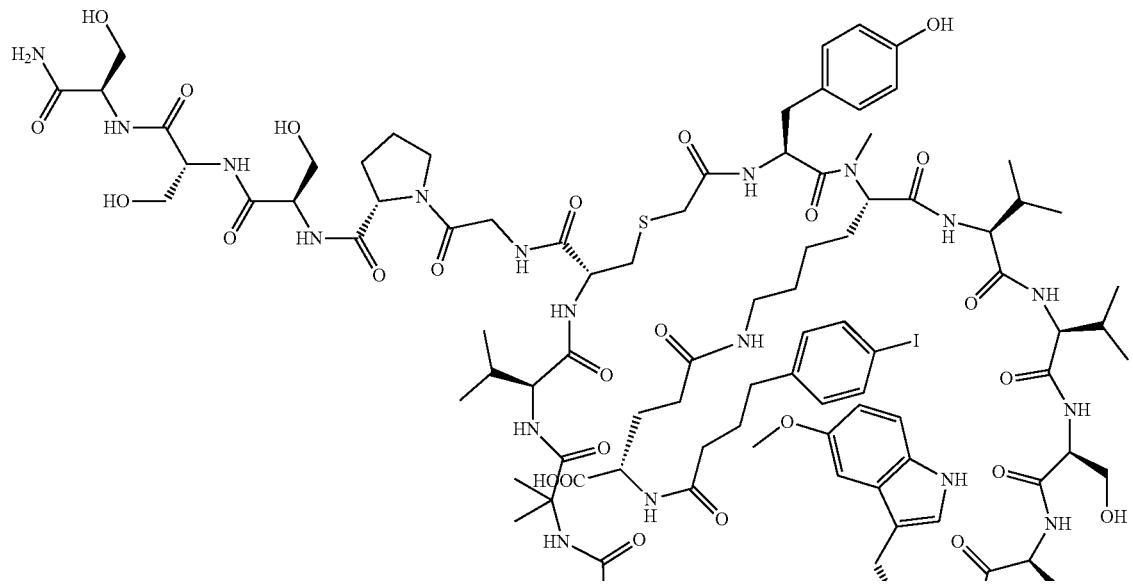

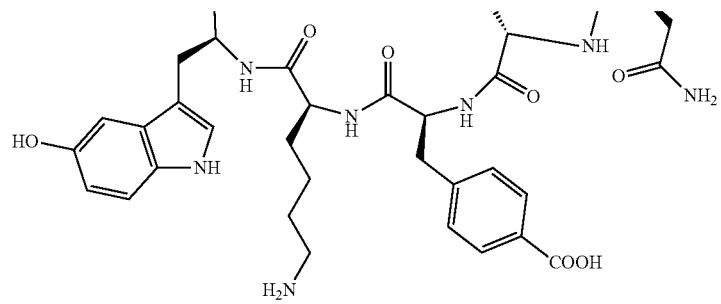

(4-(4-iodophenyl) butanoyl)-L-glutamic acid, 8 equivalents of DIC, and 4 equivalents of Oxyma pure in DMF. The resin was washed three times with DMF and DCM and then dried.

A trifluoroacetic acid (TFA)-water-triisopropylsilane (TIS)-3,6-Dioxa-1,8-octanedithiol (DODT) mixture (92.5:2.5:2.5:2.5 v/v/v/v) was added and the resulting mixture was stirred at room temperature for 1.5 hours.

The crude peptide was cleaved from resin was collected by ether precipitation. After washing three times with diisopropyl ether and drying, a DMSO-water-MeCN (1:1:1 v/v/v) containing 15 equivalents of triethylamine was added to give a final concentration of 5 mM, followed by stirring at room temperature for 2 hours. The crude peptide was confirmed by analysis conditions by LCMS: retention time=1.55 min.

The crude peptide was purified by the reverse-phase HPLC and the product was confirmed as shown in the following by HPLC under the conditions. Analysis HPLC condition: retention time=4.236 min. MS (ESI+); calcd. for $[M+2H]^{2+}$ 1302.0, found 1302.6.

Synthesis of PD-224 (Table 1-2 Compound No. 36); Compound Including Albumine Binder (E-4IPhpCO) Conjugated Monocyclic Peptide (Peptide SEQ ID No.: 23)

[CHEM 4]

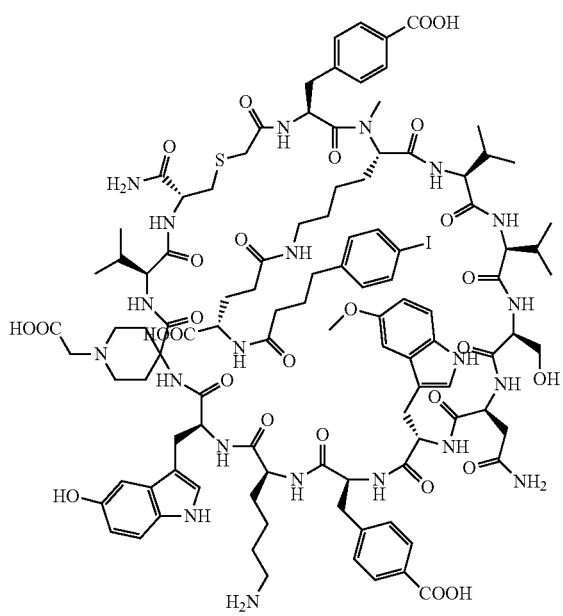

PD-224 was prepared with the same procedure described as PD-209. Double coupling was conducted at position 1 and 3 from N-terminal amino acid.

Fmoc amino acids used in the synthesis included Fmoc-Cys(Trt)-OH; Fmoc-Val-OH; Fmoc-A4pipaa(tBu)-OH; Fmoc-W5H-OH; Fmoc-Lys(Boc)-OH; Fmoc-F4COO(tBu)-OH; Fmoc-W5OMe-OH; Fmoc-Asn(Trt)-OH; Fmoc-Ser(tBu)-OH; Fmoc-N-Me-Lys(alloc)-OH.

The final product was confirmed as shown in the following by HPLC under the following conditions.

Analysis HPLC condition: retention time=3.812 min. MS (ESI+); calcd. for $[M+2H]^{2+}$1158.0, found 1158.5.

Example 4—Binding Activity of hGhR Binding Peptide Using Surface Plasmon Resonance (SPR)

SPR assay was performed using Biacore T200 (cytiva: Former GE Healthcare). After the equilibration of Series S Sensor Chip CM5 (produced by cytiva: Former GE Healthcare) with Running Buffer (HBS-EP with 1% (v/v) DMSO), an EDC/NHS mixture was injected at a flow rate of 10 μL/min for 7 minutes to thereby activate the functional groups on sensor chip. Recombinant human GhR-Fc protein (R&D Systems) in 10 mM Acetate (pH 4.0) was injected immobilized to at a flow rate of 5 μL/min. It took 7 minutes to immobilize the GhR on the substrate surfaces of the sensor chip. Then Ethanolamine was injected at a flow rate of 10 μL/min for 7 minutes. 1M Ethanolamine (aq.) was injected at a flow rate of 10 μL/min for 420 seconds for capping. 10 mM Peptides in DMSO were diluted to obtain 10 uM with Running Buffer, and prepared 100 nM, 50 nM, 25 nM, 10 nM, 5 nM of each peptide solutions (Peptide Samples).

Using these Peptide Samples, kinetics of peptides against human GhR-Fc protein were measured. The method adopted for sample measurement was a single-cycle kinetics method. The analysis was conducted using the evaluation software provided with Biacore T200. A DMSO correction curve obtained by solvent correction measurements was applied for the analysis. Kinetics fitting was done on the difference data obtained by subtracting the baseline data from sample measurement data. KD values were calculated based on the association rate constant (ka) and dissociation rate constant (kd). The results obtained are shown in the Tables 1, 2 and 3.

"PEPTIDE SEQ ID NO." in Tables 1, 2 and 3 indicates each SEQ ID NO. described in the sequence listing, and this indicates that the cyclic peptide of the compound thereof has the amino acid sequence of the applicable SEQ ID NO. Furthermore, "Linker" indicates Lysine (Lys), Glycine (Gly), or the SEQ ID NO. described in the sequence listing, and this indicates that the linker having the amino acid sequence indicated is bound. "Albumin Binder" indicates a structure containing an albumin binder bound to the cyclic peptide thereof. Note that when "NO" is stated, this indicates that the Compound does not contain this structure. Although synthesis is shown in separate examples, all the peptides in Tables 1, 2 and 3 are cyclic peptides in which the first amino acid residue and the thirteenth cysteine residue (C) are bound, and they have a structure in which a linker has the amino acid Lysine (Lys), Glycine (Gly), or the SEQ ID NO. stated in "Linker", which is further bound to the cysteine residue thereof.

"KD" in the table is a value whereby the binding test result between the Compound and hGhR using SPR is expressed in KD, and the unit is nM. Furthermore, "obs. m/z [M+2H]2+" indicates the ESI-MS(+) observed value. Unless otherwise specified, this is bivalent ($[M+2H]^{2+}$).

In Table 1, "Albumin Binder" indicates the type of albumin binder bound to the amino group of the lysine side chain positioned at the N-terminal of the linker. For example, when (E_E_4IPhoCO) is stated, this indicates that an albumin binder called 4IphpCO is bound to the amino group of the lysine side chain positioned at the N-terminal of the linker through two glutamic acids. Note that NO is stated for Compound Nos. 1 to 4 in "Albumin Binder", which indicates that these Compounds do not contain an albumin binder.

Furthermore, Compound Nos. 1 to 32 and 58 to 65 stated in Table 1 are all bicyclic peptides in which the amino group of the side chain of N-methyllysine, which is the second amino acid residue (X2), is bound to W1aa, which is the seventh amino acid residue (X7) (Compound Nos. 2, 5 to 32, and 58 to 65), or in which G/MeG/P is bound to the amino group of the side chain of the same N-methyllysine and the amino acids are further bound to W1aa, which is the seventh amino acid residue (X7) (Compound Nos. 1 to 4).

In Table 2, "Albumin Binder" indicates the type of albumin binder bound to the amino group of the side chain of N-methyllysine, which is the second amino acid residue (X2). For example, when (E_4IPhpCO) is stated in "Albumin Binder", this indicates that the albumin binder called 4IphpCO is bound to the amino group of the side chain of lysine, which is the second amino acid residue, through one glutamic acid. Furthermore, NO is stated in "Linker" for Compound Nos. 33 to 40, 43 to 45, 47, 50, and 53, which means that they do not contain a linker. Note that Compound Nos. 33 to 57 stated in Table 2 are all monocyclic peptides.

As demonstrated in Tables 1 and 2, all of compound can effectively bind to human GhR-Fc protein. Also it indicates that addition of albumin binders to the peptides does not affect their binding activity.

TABLE 1

GhR synthesised peptides

| Compound No. | Sample Name | PEPTIDE SEQ ID No. | Linker | Albumin Binder | KD (nM) | obs. m/z [M + 2H]2+ |
|---|---|---|---|---|---|---|
| 1 | GhR_PD_139 | 2 | Gly | NO | 0.7 | 913.99 |
| 2 | GhR_PD_140 | 3 | Gly | NO | 1.22 | 942.53 |
| 3 | GhR_PD_141 | 4 | Gly | NO | 1.71 | 949.52 |
| 4 | GhR_PD_142 | 5 | Gly | NO | 1.07 | 962.56 |
| 5 | GhR_PD_219 | 6 | 33 | (E_E_4IPhpCO) | 3.07 | 1249.58 |
| 6 | GhR_PD_220 | 7 | 33 | (E_E_4IPhpCO) | 1.82 | 1242.10 |
| 7 | GhR_PD_221 | 8 | Lys | (E_E_4IPhpCO) | 0.96 | 1263.64 |
| 8 | GhR_PD_250 | 9 | Lys | (E_E_4IPhpCO) | 2.08 | 1292.14 |
| 9 | GhR_PD_217 | 10 | Lys | (E_E_4IPhpCO) | 1.46 | 1242.58 |
| 10 | GhR_PD_218 | 10 | Lys | (E_E_PhpCO) | 2.03 | 1179 59 |
| 11 | GhR_PD_233 | 10 | Lys | (E-E- cC 14COO) | 2.85 | 1240.79 |
| 12 | GhR_PD_245 | 10 | Lys | (E_E_4MePhpCO) | 1.95 | 1186.64 |
| 13 | GhR_PD_247 | 10 | Lys | (E_4IPhpC0) | 1.36 | 1178.05 |
| 14 | GhR_PD_248 | 10 | 33 | (E-E_4IPhpCO) | 1.88 | 1450.25 |
| 15 | GhR_PD_253 | 10 | Lys | (E-E Biph4pCO) | 1.61 | 1217.72 |
| 16 | GhR_PD_254 | 10 | Lys | (EEPhPeCO) | 1.93 | 1193.70 |
| 17 | GhR_PD_235 | 11 | Lys | (E-E- cC 14COO) | 4.10 | 1311.85 |
| 18 | GhR_PD_238 | 12 | Lys | (E-E- cC 14COO) | 2.40 | 1276.20 |
| 19 | GhR_PD_231 | 13 | Lys | (E-E- cC 14COO) | 1.93 | 1226.70 |
| 20 | GhR_PD_241 | 13 | 33 | (E-E- cC 14COO) | 1.25 | 1434.42 |
| 21 | GhR_PD_215 | 13 | Lys | (E_E_4IPhpCO) | 1.07 | 1228.57 |
| 22 | GhR_PD_236 | 15 | Lys | (E-E- cC 14COO) | 11.22 | 1311.75 |
| 23 | GhR_PD_239 | 16 | Lys | (E-E- cC 14COO) | 2.29 | 1276.25 |
| 24 | GhR_PD_232 | 17 | Lys | (E-E- cC 14COO) | 2.59 | 1226.64 |
| 25 | GhR_PD_242 | 17 | 33 | (E-E- cC 14COO) | 2.23 | 1434.43 |
| 26 | GhR_PD_216 | 17 | Lys | (E_E_4IPhpCO) | 1.59 | 1228.60 |
| 27 | GhR_PD_234 | 18 | Lys | (E-E- cC 14COO) | 1.79 | 1297.80 |
| 28 | GhR_PD_243 | 18 | 33 | (E-E- cC 14COO) | 2.71 | 1003.93* |
| 29 | GhR_PD_237 | 19 | Lys | (E-E- cC 14COO) | 1.57 | 1262.36 |
| 30 | GhR_PD_244 | 19 | 33 | (E-E- cC 14COO) | 2.26 | 1469.90 |
| 31 | GhR_PD_240 | 2 | 33 | (E-E- cC 14COO) | 0.92 | 1420.39 |
| 32 | GhR_PD_246 | 2 | Lys | (E_E_4IPhpCO) | 0.98 | 1214.57 |
| 58 | GhR_PD_267 | 10 | Lys | (E-E-Ac) | 3.51 | 1127.60 |
| 59 | GhR_PD_268 |  | Lys | (E-E-cC12COO) | 2.98 | 1226.76 |
| 60 | GhR_PD_269 | 10 | Lys | (E-E-cC13COO) | 3.10 | 1233.77 |
| 61 | GhR_PD_270 | 10 | Lys | (E-E-cC15COO) | 2.53 | 1247.80 |
| 62 | GhR_PD_271 | 10 | Lys | (PEG2Ac-PEG2Ac-E-E- | 3.88 | 1371.95 |
| 63 | GhR_PD_272 | 10 | Lys | (PEG2Ac-PEG2Ac-E-E-cC13COO | 3.70 | 1379.00 |
| 64 | GhR_PD_273 | 10 | Lys | (PEG2Ac-PEG2Ac-E-E-cC14COO | 3.61 | 1386.05 |
| 65 | GhR_PD_274 | 10 | Lys | (PEG2Ac-PEG2Ac-E-E-cC15COO | 3.33 | 1392.95 |

*means obs. m/z [M + 3H]3+

TABLE 2

GhR synthesised peptides

| Compound No. | Sample Name | PEPTIDE SEQ ID No. | Linker | Albumin Binder | KD (nM) | obs. m/z [M + 2H]2+ |
|---|---|---|---|---|---|---|
| 33 | GhR_PD_204 | 20 | NO | (E-4IPhpCO) | 9.43 | 1073.03 |
| 34 | GhR_PD_202 | 21 | NO | (E-4IPhpCO) | 2.77 | 1087.36 |
| 35 | GhR_PD_223 | 22 | NO | (E-4IPhpCO) | 5.47 | 1194.08 |
| 36 | GhR_PD_224 | 23 | NO | (E-4IPhpCO) | 10.82 | 1158.48 |
| 37 | GhR_PD_255 | 23 | NO | (E-BiPh4pCO) | 5.81 | 1133.64 |
| 38 | GhR_PD_256 | 23 | NO | (E-PhPeCO) | 2.82 | 1109.54 |
| 39 | GhR_PD_208 | 24 | NO | (E-4IPhpCO) | 2.19 | 1108.89 |
| 40 | GhR_PD_212 | 24 | NO | (E-E-4IPhpCO) | 2.96 | 1173.46 |
| 41 | GhR_PD_210 | 24 | 32 | (E-4IPhpCO) | 2.63 | 1316.60 |
| 42 | GhR_PD_214 | 24 | 32 | (E-E-4IPhpCO) | 3.79 | 1381.16 |
| 43 | GhR_PD_203 | 25 | NO | (E-4IPhpCO) | 3.95 | 1080.39 |
| 44 | GhR_PD_206 | 26 | NO | (E-4IPhpCO) | 9.67 | 1165.98 |
| 45 | GhR_PD_205 | 27 | NO | (E-4IPhpCO) | 3.36 | 1130.50 |
| 46 | GhR_PD_207 | 28 | 32 | (E-4IPhpCO) | 1.07 | 1288.55 |
| 47 | GhR_PD_227 | 29 | NO | (E-E-4IPhpCO) | 7.38 | 1244.52 |
| 48 | GhR_PD_225 | 29 | 34 | (E-4IPhpCO) | 4.35 | 1387.75 |
| 49 | GhR_PD_229 | 29 | 32 | (E-E-4IPhpCO) | 6.31 | 1452.28 |
| 50 | GhR_PD_228 | 30 | NO | (E-E-4IPhpCO) | 4.13 | 1209.09 |
| 51 | GhR_PD_226 | 30 | 32 | (E-4IPhpCO) | 7.57 | 1352.14 |
| 52 | GhR_PD_230 | 30 | 32 | (E-E-4IPhpCO) | 5.47 | 1416.78 |
| 53 | GhR_PD_211 | 31 | NO | (E-E-4IPhpCO) | 3.36 | 1159.49 |
| 54 | GhR_PD_209 | 31 | 32 | (E-4IPhpCO) | 2.08 | 1302.61 |
| 55 | GhR_PD_213 | 31 | 32 | (E-E-4IPhpCO) | 2.83 | 1367.15 |
| 56 | GhR_PD_251 | 31 | 32 | (E-Biph4pCO) | 2.87 | 1277.78 |
| 57 | GhR_PD_252 | 31 | 32 | (E-PhPeCO) | 1.25 | 1253.75 |

1-(tert-butyl) 5-(2,5-dioxopyrrolidin-1-yl) ((S)-5-(tert-butoxy)-4-(4-(4-iodophenyl)butanamido)-5-oxopentanoyl)-L-glutamate

[CHEM 5]

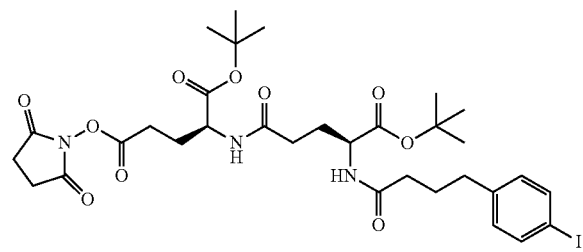

3-(((ethylimino)methylene)amino)-N,N-dimethylpropan-1-amine hydrochloride (4.22 g, 22.00 mmol) was added to a solution of 4-(4-iodophenyl)butanoic acid (5.80 g, 20 mmol) and 1-hydroxypyrrolidine-2,5-dione (2.76 g, 24.00 mmol) in DCM (40.0 ml) and the mixture was stirred at 0 deg. C. for 1 h. The solution was quenched with 1 N HCl aqueous solution, extracted with DCM twice. The combined organic layer was washed with brine, dried over Na₂SO₄ and the filtrate was dried under reduced pressure.

Solution of obtained residue and DIPEA (6.99 ml, 40.0 mmol) in DMF (40.0 ml) was stirred at room temperature overnight. The solution was diluted with EtOAc, extracted with 1 N HCl aqueous solution, washed with EtOAc twice. The combined organic layer was washed with water and brine, dried over Na₂SO₄ and the filtrate was dried under reduced pressure.

The crude residue was purified by flash column chromatography (0% to 10% MeOH in DCM) to obtain a light yellow oil.

EDC (4.22 g, 22.00 mmol) was added to a solution of the light yellow oil obtained above and 1-hydroxypyrrolidine-2,5-dione (2.53 g, 22.00 mmol) in DCM (66.7 ml) and the mixture was stirred at 0 deg. C. for 1 h. The solution was quenched with 1 N HCl aqueous solution, extracted with DCM twice. The combined organic layer was washed with saturated NaHCO₃ aqueous solution, water and brine, dried over Na₂SO₄ and the filtrate was dried under reduced pressure.

A solution of the crude product, 1-(tert-butyl) 5-(2,5-dioxopyrrolidin-1-yl) (4-(4-iodophenyl)butanoyl)-L-glutamate and N-ethyl-N-isopropylpropan-2-amine (5.17 g, 40.0 mmol) in DMF (67 ml) was stirred at room temperature overnight. The solution was diluted with EtOAc, extracted with 1 N HCl aqueous solution, washed with EtOAc twice. The combined organic layer was washed with water and brine, dried over Na₂SO₄ and the filtrate was dried under reduced pressure to give a light yellow oil.

To a solution of the light yellow oil and 1-hydroxypyrrolidine-2,5-dione (2.014 g, 17.50 mmol) in DCM (28.0 ml) was added 3-(((ethylimino)methylene)amino)-N,N-dimethylpropan-1-amine hydrochloride (3.35 g, 17.50 mmol) and the mixture was stirred at 0 deg. C. for 1 h. The solution was quenched with 1:1 mixture of 1 N HCl aqueous solution and brine, extracted with DCM twice. The combined organic layer was dried over Na₂SO₄ and the filtrate was dried under reduced pressure to give the titled compound as a white solid. Analysis by LCMS: MS (ESI+); calcd. for [M+H]⁺ 758.2, found 758.4.

The present technology may be used in bio-related industries and the pharmaceutical industry.

All references cited in this specification, and their references, are incorporated by reference herein in their entirety where appropriate for teachings of additional or alternative details, features, and/or technical background.

While the disclosure has been particularly shown and described with reference to particular embodiments, it will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

The invention claimed is:

1. A peptide or a salt thereof consisting of the following amino acid sequence:

(SEQ ID NO: 1)
X1-X2-X3-X4-X5-X6-X7-X8-X9-X10-X11-X12-X13 wherein:
X1 is an amino acid having an aromatic ring;
X2 is N-methyl-L-lysine (MeK);
X3 and X4 are each valine;
X5 is serine;
X6 is asparagine;
X7 is tryptophan, 1-(carboxymethyl)-L-tryptophan (W1aa), 5-Methoxy-L-tryptophan (W5OMe), or 5-Hydroxy-L-Tryptophan (W5H);
X8 is phenylalanine, 4-Carboxy-L-Phenylalanine (F4COO));
X9 is lysine, N6-carbamimidoyl-L-lysine (Har), N6-(4-(carboxymethyl) piperazine-1-carbonyl)-L-lysine (KCOpipzaa), N-Methyl-L-Lysine (MeK), (S)-2,6-diamino-6-oxohexanoic acid (Hgn), (s)-2-aminoheptanic acid (Ahp), or arginine;
X10 is 5-hydroxy-L-tryptophan (W5H);
X11 is alpha-methyl alanine (Aib) or 4-amino-1-(carboxymethyl) piperidine-4-carboxylic acid (A4pipaa);
X12 is valine; and
X13 is cysteine; and
wherein the peptide or the salt thereof comprises none, one, two or three conservative amino acid substitution, and wherein the peptide or the salt thereof has avidity for a growth hormone receptor (GhR).

2. The peptide or the salt thereof according to claim 1, wherein X7 is 1-(carboxymethyl)-L-tryptophan (W1aa); and the amino acid residues of X2 and X7 are bound.

3. The peptide or the salt thereof according to claim 1, wherein an albumin binder is bound to X2.

4. The peptide or the salt thereof according to claim 3, wherein the albumin binder is 4IphpCO, Biph4pCO, PhPeCO, PhpCO, cC14COO, or 4MePhpCO.

5. The peptide or the salt thereof according to claim 2, wherein:
X1 is Y, 4-pyridyl-L-alanine (4Py), or F4COO;
X8 is Y or F4COO; and
X9 is K, KCOpipzaa, Hgn, Ahp, or Har.

6. The peptide or the salt thereof according to claim 1, wherein the peptide or the salt thereof has a sequence represented by F4COO-MeK-V-V-S-N-W1aa-F4COO-K-W5H-Aib-V-C(SEQ ID NO: 10);
wherein the second and seventh amino acid residues in SEQ ID NO: 10 are bound; and
wherein the peptide or the salt thereof has avidity for human growth factor receptor (hGhR).

7. The peptide or the salt thereof according to claim 1, wherein the peptide or the salt thereof has a sequence represented by Y-MeK-V-V-S-N-W5OMe-F4COO-K-W5H-A4pipaa-V-C(SEQ ID NO: 30);
wherein an albumin binder is bound to MeK; and
wherein the peptide or the salt thereof has avidity for hGhR.

8. The peptide or the salt thereof according to claim 7, wherein the albumin binder is 4IphpCO, Biph4pCO, PhPeCO, PhpCO, cC14COO, or 4MePhpCO.

9. The peptide or the salt thereof according to claim 1, wherein the peptide or the salt thereof is a cyclic peptide.

10. The peptide or the salt thereof according to claim 9, wherein the peptide or the salt thereof has a cyclic structure having a chloroacetylated amino acid in X1 and a cysteine residue; and wherein the chloroacetylated amino acid in X1 and the cysteine residue are bound.

11. The peptide or the salt thereof according to claim 1, wherein the peptide or the salt thereof consists of an amino acid sequence selected from SEQ ID NOs: 2 to 9, 11 to 29, and 31.

12. The peptide or the salt thereof according to claim 1, wherein the peptide or the salt thereof consists of an amino acid sequence selected from SEQ ID NOs: 2 to 9, 11 to 29 and 31 to which a linker is added in C-terminus.

13. The peptide or the salt thereof according to claim 12, wherein the linker comprises an amino acid sequence selected from Lysine, and SEQ ID NO: 33.

14. The peptide or the salt thereof according to claim 1, wherein the peptide or the salt thereof has human growth hormone receptor (hGhR) antagonistic activity.

15. A pharmaceutical composition containing the peptide or the salt thereof according to claim 1, and a pharmaceutically acceptable carrier, excipient, or additive.

16. The pharmaceutical composition according to claim 15, wherein the pharmaceutical composition has hGhR antagonistic activity.

17. The peptide or the salt thereof according to claim 1, wherein X1 is Y, 4Py, or F4COO.

* * * * *

```
                              SEQUENCE LISTING

<160> NUMBER OF SEQ ID NOS: 33

<210> SEQ ID NO 1
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (1)..(13)
<223> OTHER INFORMATION: Xaa can be any naturally occurring amino acid

<400> SEQUENCE: 1

Xaa Xaa Xaa Xaa Xaa Xaa Xaa Xaa Xaa Xaa Xaa Xaa Xaa
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha- Methyl Alanine

<400> SEQUENCE: 2

Tyr Lys Val Val Ser Asn Xaa Tyr Lys Xaa Xaa Val Cys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: BINDING
<222> LOCATION: (2)..(2)
<223> OTHER INFORMATION: Glycine
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
```

```
<222> LOCATION: (11)..(11)
<223> OTHER INFORMATION: Xaa is Alpha-Methyl Alanine

<400> SEQUENCE: 3

Tyr Lys Val Val Ser Asn Xaa Tyr Lys Xaa Xaa Val Cys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: BINDING
<222> LOCATION: (2)..(2)
<223> OTHER INFORMATION: N-methylglycine
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 4

Tyr Lys Val Val Ser Asn Xaa Tyr Lys Xaa Xaa Val Cys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: BINDING
<222> LOCATION: (2)..(2)
<223> OTHER INFORMATION: Proline
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 5

Tyr Lys Val Val Ser Asn Xaa Tyr Lys Xaa Xaa Val Cys
1               5                   10

<210> SEQ ID NO 6
<211> LENGTH: 13
<212> TYPE: PRT
<213> ORGANISM: Artificial Sequence
```

```
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (9)..(9)
<223> OTHER INFORMATION: Xaa is (S)-2,6-diamino-6-oxohexanoic acid
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 6

Xaa Lys Val Val Ser Asn Xaa Xaa Xaa Xaa Xaa Val Cys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (9)..(9)
<223> OTHER INFORMATION: Xaa is (s)-2-aminoheptanic acid
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 7

Xaa Lys Val Val Ser Asn Xaa Xaa Xaa Xaa Xaa Val Cys
1               5                   10

<210> SEQ ID NO 8
```

```
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (9)..(9)
<223> OTHER INFORMATION: Xaa is N6-carbamimidoyl-L-lysine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 8

Xaa Lys Val Val Ser Asn Xaa Xaa Xaa Xaa Xaa Val Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is 4-Amino-1-(carboxymethyl) piperidine-4-
      carboxylic acid

<400> SEQUENCE: 9

Xaa Lys Val Val Ser Asn Xaa Xaa Lys Xaa Xaa Val Cys
1               5                   10

<210> SEQ ID NO 10
```

```
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 10

Xaa Lys Val Val Ser Asn Xaa Xaa Lys Xaa Xaa Val Cys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (9)..(9)
<223> OTHER INFORMATION: Xaa is N6-(4-(carboxymethyl) piperazine-1-
      carbonyl)-L-lysine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 11

Xaa Lys Val Val Ser Asn Xaa Tyr Xaa Xaa Xaa Val Cys
1               5                   10

<210> SEQ ID NO 12
<211> LENGTH: 13
<212> TYPE: PRT
<213> ORGANISM: Artificial Sequence
<220> FEATURE:
```

-continued

```
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is 4-Amino-1-(carboxymethyl) piperidine-4-
      carboxylic acid

<400> SEQUENCE: 12

Xaa Lys Val Val Ser Asn Xaa Tyr Lys Xaa Xaa Val Cys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 13

Xaa Lys Val Val Ser Asn Xaa Tyr Lys Xaa Xaa Val Cys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 5-[(2S)-2-amino-2-carboxyethyl]pyridine-
      2-carboxylic acid
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
```

```
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (8)..(8)
<223> OTHER INFORMATION: Xaa is 5-[(2S)-2-amino-2-carboxyethyl]pyridine-
      2-carboxylic acid
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 14

Xaa Lys Val Val Ser Asn Xaa Xaa Lys Xaa Xaa Val Cys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (9)..(9)
<223> OTHER INFORMATION: Xaa is N6-(4-(carboxymethyl) piperazine-1-
      carbonyl)-L-lysine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 15

Tyr Lys Val Val Ser Asn Xaa Xaa Xaa Xaa Xaa Val Cys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
```

```
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is 4-Amino-1-(carboxymethyl) piperidine-4-
      carboxylic acid

<400> SEQUENCE: 16

Tyr Lys Val Val Ser Asn Xaa Xaa Lys Xaa Xaa Val Cys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 17

Tyr Lys Val Val Ser Asn Xaa Xaa Lys Xaa Xaa Val Cys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (9)..(9)
<223> OTHER INFORMATION: Xaa is N6-(4-(carboxymethyl) piperazine-1-
      carbonyl)-L-lysine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 18

Tyr Lys Val Val Ser Asn Xaa Tyr Xaa Xaa Xaa Val Cys
```

<210> SEQ ID NO 19
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 1-(Carboxymethyl)-L-Tryptophan
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is 4-Amino-1-(carboxymethyl) piperidine-4-carboxylic acid

<400> SEQUENCE: 19

Tyr Lys Val Val Ser Asn Xaa Tyr Lys Xaa Xaa Val Cys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-pyridyl-L-alanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is (S)-2-amino-3-(1H-pyrrolo[2,3-b]pyridin-3-yl)propanoic acid
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 20

Xaa Lys Val Val Ser Asn Xaa Xaa Lys Xaa Xaa Val Cys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE

```
<222> LOCATION: (1)..(1)
<223> OTHER INFORMATION: Xaa is 4-pyridyl-L-alanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 5-Methoxy-L-tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 21

Xaa Lys Val Val Ser Asn Xaa Xaa Lys Xaa Xaa Val Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 5-Methoxy-L-tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (9)..(9)
<223> OTHER INFORMATION: Xaa is N6-(4-(carboxymethyl) piperazine-1-
      carbonyl)-L-lysine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 22

Xaa Lys Val Val Ser Asn Xaa Xaa Xaa Xaa Xaa Val Cys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
```

```
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 5-Methoxy-L-tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is 4-Amino-1-(carboxymethyl) piperidine-4-
      carboxylic acid

<400> SEQUENCE: 23

Xaa Lys Val Val Ser Asn Xaa Xaa Lys Xaa Xaa Val Cys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (1)..(1)
<223> OTHER INFORMATION: Xaa is 4-Carboxy-L-Phenylalanine
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 5-Methoxy-L-tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 24

Xaa Lys Val Val Ser Asn Xaa Xaa Lys Xaa Xaa Val Cys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
```

-continued

```
<222> LOCATION: (7)..(7)
<223> OTHER INFORMATION: Xaa is (S)-2-amino-3-(1H-pyrrolo[2,3-b]pyridin-
      3-yl)propanoic acid
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 25

Tyr Lys Val Val Ser Asn Xaa Xaa Lys Xaa Xaa Val Cys
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 5-Methoxy-L-tryptophan
<220> FEATURE:
<221> NAME/KEY: MISC_FEATURE
<222> LOCATION: (9)..(9)
<223> OTHER INFORMATION: Xaa is N6-(4-(carboxymethyl) piperazine-1-
      carbonyl)-L-lysine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 26

Tyr Lys Val Val Ser Asn Xaa Tyr Xaa Xaa Xaa Val Cys
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 5-Methoxy-L-tryptophan
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is 4-Amino-1-(carboxymethyl) piperidine-4-
      carboxylic acid
```

```
<400> SEQUENCE: 27

Tyr Lys Val Val Ser Asn Xaa Tyr Lys Xaa Xaa Val Cys
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 5-Methoxy-L-tryptophan
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 28

Tyr Lys Val Val Ser Asn Xaa Tyr Lys Xaa Xaa Val Cys
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 5-Methoxy-L-tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (9)..(9)
<223> OTHER INFORMATION: Xaa is N6-(4-(carboxymethyl) piperazine-1-
      carbonyl)-L-lysine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 29

Tyr Lys Val Val Ser Asn Xaa Xaa Xaa Xaa Xaa Val Cys
1               5                   10

<210> SEQ ID NO 30
<211> LENGTH: 13
<212> TYPE: PRT
<213> ORGANISM: Artificial Sequence
<220> FEATURE:
```

```
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 5-Methoxy-L-tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is 4-Amino-1-(carboxymethyl) piperidine-4-
      carboxylic acid

<400> SEQUENCE: 30

Tyr Lys Val Val Ser Asn Xaa Xaa Lys Xaa Xaa Val Cys
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthesized polypeptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (7)..(7)
<223> OTHER INFORMATION: Xaa is 5-Methoxy-L-tryptophan
<220> FEATURE:
<221> NAME/KEY: MISC_FEATURE
<222> LOCATION: (8)..(8)
<223> OTHER INFORMATION: Xaa is 4-Carboxy-L-Phenylalanine
<220> FEATURE:
<221> NAME/KEY: MISC_FEATURE
<222> LOCATION: (10)..(10)
<223> OTHER INFORMATION: Xaa is 5-Hydroxy-L-Tryptophan
<220> FEATURE:
<221> NAME/KEY: MISC_FEATURE
<222> LOCATION: (11)..(11)
<223> OTHER INFORMATION: Xaa is Alpha-Methyl Alanine

<400> SEQUENCE: 31

Tyr Lys Val Val Ser Asn Xaa Xaa Lys Xaa Xaa Val Cys
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (3)..(3)
<223> OTHER INFORMATION: Xaa is D-Serine
<220> FEATURE:
<221> NAME/KEY: MISC_FEATURE
<222> LOCATION: (4)..(4)
<223> OTHER INFORMATION: Xaa is D-Serine
<220> FEATURE:
<221> NAME/KEY: MISC_FEATURE
<222> LOCATION: (5)..(5)
```

```
<223> OTHER INFORMATION: Xaa is D-Serine

<400> SEQUENCE: 32

Gly Pro Xaa Xaa Xaa
1               5

<210> SEQ ID NO 33
<211> LENGTH: 6
<212> TYPE: PRT
<213> ORGANISM: Artificial Sequence
<220> FEATURE:
<223> OTHER INFORMATION: Synthesized polypeptide
<220> FEATURE:
<221> NAME/KEY: MISC_FEATURE
<222> LOCATION: (3)..(3)
<223> OTHER INFORMATION: Xaa is D-Serine
<220> FEATURE:
<221> NAME/KEY: MISC_FEATURE
<222> LOCATION: (4)..(4)
<223> OTHER INFORMATION: Xaa is D-Serine
<220> FEATURE:
<221> NAME/KEY: MISC_FEATURE
<222> LOCATION: (5)..(5)
<223> OTHER INFORMATION: Xaa is D-Serine

<400> SEQUENCE: 33

Gly Pro Xaa Xaa Xaa Lys
1               5
```